US006492124B1

United States Patent
Wong et al.

(10) Patent No.: US 6,492,124 B1
(45) Date of Patent: Dec. 10, 2002

(54) TRANCE ACTIVATED SIGNAL TRANSDUCTION PATHWAYS IN OSTEOCLASTS

(75) Inventors: Brian Wong, New York, NY (US); Daniel Besser, New York, NY (US); Yongwon Choi, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/330,867

(22) Filed: Jun. 11, 1999

(51) Int. Cl.$^7$ ............... G01N 33/567; A61K 38/00; C07K 14/00
(52) U.S. Cl. ............... 435/7.1; 514/2; 530/350
(58) Field of Search ............... 435/7.1; 514/2; 530/330

(56) References Cited

U.S. PATENT DOCUMENTS

| 5,599,681 A | 2/1997 | Epstein et al. |
| 5,843,678 A | 12/1998 | Boyle |

FOREIGN PATENT DOCUMENTS

| WO | WO 98/28426 | 7/1998 |
| WO | WO 99/29865 | 6/1999 |

OTHER PUBLICATIONS

Ozes et al. Nature, vol. 401, pp. 82–85, 1999.*
Rothe et al., Cell, 78:681–692, (1994).
Soriano et al., Cell, 64:693–702, (1991).
Lacey et al., Cell, 93:165–176, (1998).
Darnay et al., J. Biol. Chem., 274:7724–7731, (1999).
Bachmann et al., J. Exp. Med.: 189, 1025–1031, (1999).
Arch et al., Genes Dev., 12:2821–2830, (1998).
Thomas et al., Annu. Rev. Cel. Dev. Biol., 13:513–609, (1997).
Lavagna–Sevenier et al., Leukemia, 12:301–10, (1998).
Howlett et al., Biochem. Biophys. Res. Commun., 257:129–38, (1999).
Erdriech–Epstein et al., J. Leukoc. Biol., 65:523–34, (1999).
Danilkovitch and Leonard, J. Leukoc. Biol., 65: 345–8, (1999).
Lutz et al., Biochem. Biophys. Res. Commun. 243: 503–8, (1998).
Luca et al., Am. J. Physiol., 276: H1520–6, (1999).
Chen, Mol. Med. Today, 3:160–167, (1997).
Pear et al., Proc. Natl. Acad. Sci. U.S.A., 90:8392–8396, (1993).
Xia et al., Science, 270:1326–1331, (1995).
Schwartzberg et al., Oncogene, 17:1463–1468, (1998).
Tanaka et al., Nature, 383:528–531, (1996).
Song et al., Proc. Natl. Acad. Sci. U.S.A., 94:9792–9796, (1997).
Zha et al., Cell, 87:619–628, (1996).
Brunet et al., Cell, 96:857–868, (1999).

Medzhitov et al., Mol. Cell, 2:253–258, (1998).
Cao et al., Nature, 383:443–446, (1996).
Galibert et al., J. Biol. Chem., 273:34120–34127, (1998).
Iotsova et al., Nat. Med., 3:1285–9, (1997).
Watton and Downward, Curr. Biol., 22:433–6, (1999).
Spitz et al., Anticancer Res., 16:3415–3422, (1996).
Indolfi et al., Nat. Med., 2:634–635, (1996).
Kijima et al., Pharmacol. Ther. 68:247–267, (1995).
Inaba et al., J. Exp. Med., 176:1693–1702, (1992).
Malinin et al., Nature, 385:540–544, (1997).
Wong et al., J. Exp. Med., 186:2075–2080, (1997).
Boyce et al., J. Clin. Invest., 90:1622–1627, (1992).
Cardone et al., Science, 282:1318–1321, (1998).
Bao et al., Blood, 93: 3757–3773, (1999).
Wani, et al., Endocrinology, 140:1927–1635, (1999).
Wunderlich et al., Eur. J. Immunol., 29: 1068–75, (1999).
Coffer, et al., Biochem. J., 335:1–13, (1998).
Fuller et al., J. Exp. Med., 188:997–1001, (1998).
Wong et al., J. Biol. Chem., 272, 25190–25194, (1997).
Wong, et al., J. Biol. Chem., 273: 28355–9, (1998).
Zhang et al., J. Biol. Chem., 274:7611–7614, (1999).
Khursigara et al, J. Biol. Chem., 274: 2597–600, (1999).
Yasuda, et al., Proc. Natl. Acad. Sci. USA, 95:3597–3602, (1998).
Kong et al., Nature, 397:315–323, (1999).
Burgess, et al., J. Cell. Biol., 145:527–538, (1999).
Simonet et al., Cell, 89:309–319, (1997).
Josien et al., J. Immunol., 162:2562–2568, (1999).
Baichwal, et al., Curr. Biol., 7:R94–96, (1997).
Nishitoh, et al., Mol. Cell, 2:389–395, (1998).
Schwartzberg, et al., Genes Dev., 11:2835–2844, (1997).
Arch et al., Genes Dev., 12:2821–2830, (1998).
Lomaga, et al., Genes Dev., 13:1015–1024, (1999).
Kanagasundaram et al., Mol. Cell Biol., 19:4079–92, (1999).
Anderson et al., Nature, 390:175–179, (1997).
Fruman, et al., Annu. Rev. Biochem., 67:481–507, (1998).

* cited by examiner

Primary Examiner—Yvonne Eyler
Assistant Examiner—Janet L. Andres
(74) Attorney, Agent, or Firm—Darby & Darby

(57) ABSTRACT

The present invention relates to methods and compositions for modulating activity of a TRANCE receptor, including the modulation of TRANCE signaling activity. In particular, the invention provides screening methods by which novel modulators of TRANCE signaling may be identified, including TRANCE inhibitors, agonists and antagonists. The invention also relates to the identification of one or more specific pathways for osteoclast surivival, and the manipulation of this pathway (e.g., using a TRANCE modulator of the invention). Such manipulation may provide strategies for treating osteoclast-related diseases such as osteoporosis and osteopetrosis.

39 Claims, 8 Drawing Sheets

Osteoclasts
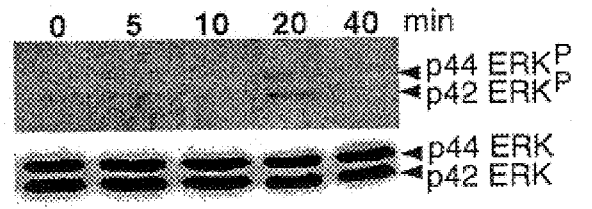
FIG. 1A
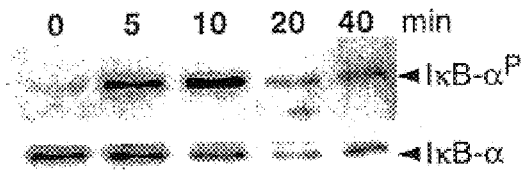
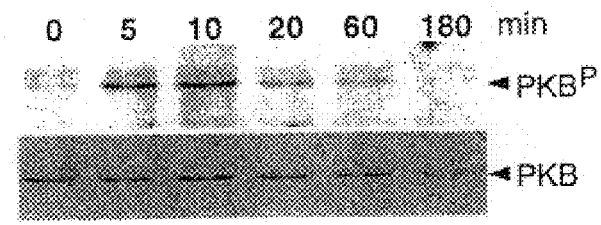
Dendritic Cells
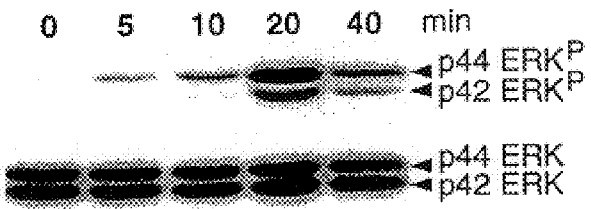
FIG. 1B
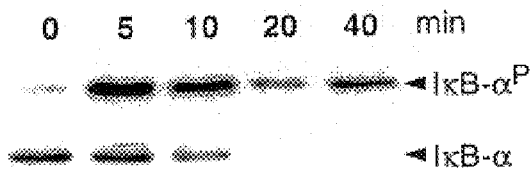
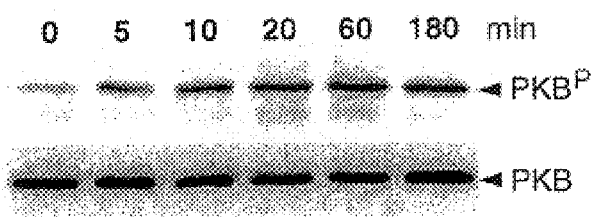

Osteoclasts

Dendritic Cells

| Ectodomain/TM | Intracellular Region | TRAF1 TRAF2 TRAF3 TRAF5 | TRAF6 | c-Src | PTK-activity |
|---|---|---|---|---|---|
| ▨ | TR-wt | + | + | + | + |
| ▨ | TR-235-358 | – | + | + | + |
| ▨ | TR-532-625 | + | – | – | – |
| ▨ | TR-354-536 | – | + | + | + |

FIG. 4E
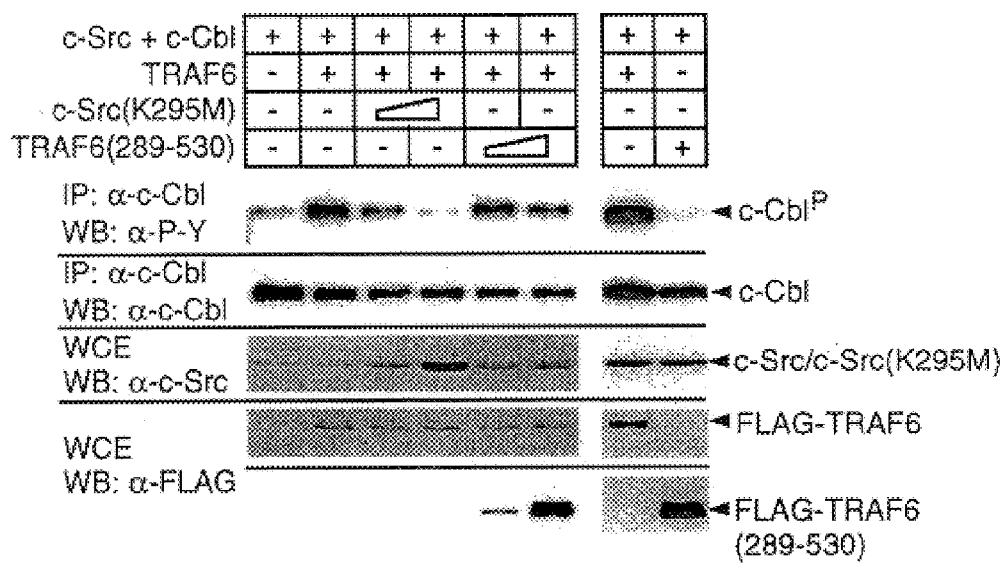
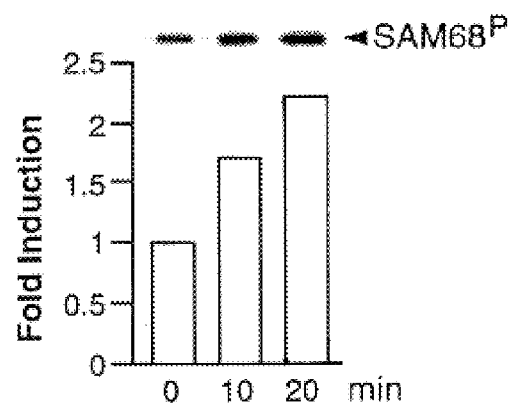
FIG. 5A
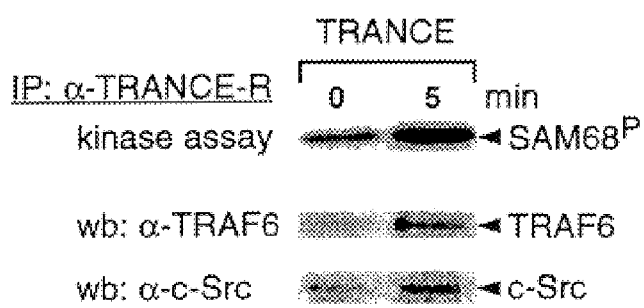
FIG. 5B

TRANCE ACTIVATED SIGNAL TRANSDUCTION PATHWAYS IN OSTEOCLASTS

The work leading to the present invention was supported, in part, by National Institute of Health Grants AI-44264, CA-523133, and CA-44356 and MSTP grant GM-07739. Thus, the United States Government has certain rights in the invention.

FIELD OF THE INVENTION

The present invention relates to the identification of the TRANCE signal transduction pathway in osteoclasts. This pathway can be exploited for high throughput screening of compounds to identify TRANCE modulators (agonists and antagonists). The invention also relates to identification of a specific pathway in osteoclast survival, and permits manipulation of this pathway, which can provide strategies for treating osteoclast-related diseases such as osteoporosis and osteopetrosis.

BACKGROUND OF THE INVENTION

Members of the tumor necrosis factor (TNF) family regulate an array of cellular responses including survival, activation, differentiation, and apoptosis. TNF-related activation-induced cytokine (TRANCE; (Wong et al., J. Biol. Chem., 272, 25190–25194, 1997) also called receptor-activator of NF-κB (RANK) ligand (RANKL), osteoclast differentiation factor (ODF) and osteoprotegerin (OPG) ligand (OPGL)) is expressed on T cell-receptor activated T cells and stimulates the TRANCE receptor (TRANCE-R/RANK) on dendritic cells to promote their survival and induce the expression of T-cell regulatory cytokines (Wong et al., supra, 1997; Wong et al., J. Exp. Med., 186:2075–2080, 1997; Josien et al., J. Immunol., 162:2562–2568, 1999). Priming of T cells is dependent on dendritic cell activation (Bachmann et al., J. Exp. Med.: 189, 1025–1031, 1999) and TRANCE appears to be critical for T-helper cell responses to certain viral infections (Bachmann, et al., supra, 1999), suggesting that TRANCE regulates dendritic cell function in vivo. Moreover, it has been shown that TRANCE regulates osteoclasts, cells of monocyte/macrophage origin which resorb calcified bone matrix, a process essential in bone development and homeostasis (Lacey, et al., Cell, 93:165–176, 1998; Yasuda, et al., Proc. Natl. Acad. Sci. U.S.A., 95::3597–3602, 1998). TRANCE is expressed on osteoblasts in response to calciotropic hormones and cytokines, and is critical for osteoclast differentiation from hematopoietic precursors (Lacey et al., supra, 1998; Yasuda, et al., supra, 1998). In mature osteoclasts, TRANCE stimulation induces cell spreading and enhances cell survival and bone resorption (Fuller et al., J. Exp. Med., 188:997–1001, 1998).

Mice with a targeted deletion in the TRANCE gene exhibit osteopetrosis, or thickening of bony matrix, due to a defect in osteoclast differentiation (Kong et al., Nature, 397:315–323, 1999). Mice with a targeted deletion of the non-receptor protein tyrosine kinase (PTK), c-Src (Soriano et al., Cell, 64:693–702, 1991) and mice doubly deficient in nuclear factor-kappa B (NF-κB)1 and NF-κB2 (Iotsova, et al., Nat. Med., 3:1285–9, 1997) also exhibit osteopetrosis. However, while osteoclasts fail to differentiate in NF-κB1 and NF-κB2 deficient mice, osteoclasts from c-Src-deficient mice develop normally but are unable to resorb bone. TRANCE is critical for osteoclast maturation and osteoclast activation (i.e., bone resorption, cytoskeletal rearrangements), suggesting a link between TRANCE, NF-κB and c-Src-mediated signaling. In contrast to its role in osteoclastogenesis, TRANCE does not appear to be important for dendritic cell differentiation since mature dendritic cells are detected at normal levels in TRANCE-deficient mice (Kong et al, supra, 1999).

Two receptors for TRANCE have been identified: OPG/OCIF, a secreted decoy receptor (Yasuda, et al., supra, 1998; Simonet et al., Cell, 89:309–319, 1997), and TRANCE-R (Wong et al., supra, 1997), identified as RANK (Anderson et al., Nature, 390:175–179, 1997), an integral membrane protein with an intracellular signaling domain. TRANCE-R, similar to other TNFR family members, lacks intrinsic catalytic activity and interacts with TNF receptor-associated factors (TRAFs) that act as adapters to activate downstream signaling pathways (Rothe et al., Cell, 78:681–692, 1994). TRANCE-R can interact with TRAF1, TRAF2, TRAF3, TRAF5 and TRAF6 when overexpressed in cell lines. TRAF1, TRAF2, TRAF3, and TRAF5 interact with a canonical PXQXT motif in the C-terminal region of the TRANCE-R cytoplasmic tail whereas TRAF6 binds to a unique motif more proximal to the transmembrane domain (Wong et al., J. Biol. Chem., 273:28355–28359, 1998; Galibert et al., J. Biol. Chem., 273:34120–34127, 1998; Darnay et al., J. Biol. Chem., 274:7724–7731, 1999). Several reports demonstrated that while TRAF2 appears important for c-Jun N-terminal kinase activation, TRAF6 is most likely the critical mediator of NF-κB activation by the TRANCE-R since TRAF6 -interacting regions of the cytoplasmic tail are necessary and sufficient for NF-κB activation (Wong et al., supra, 1998; Galibert et al., supra, 1998; Darnay et al., supra, 1999). TRAF6 also mediates NF-κB activation by interleukin-1R (Cao et al., Nature, 383:443–446, 1996; Medzhitov et al., Mol. Cell, 2:253–258, 1998), and toll-like receptors (Zhang et al., J. Biol. Chem., 274:7611–7614, 1999), indicating that TRAF6 links several families of cytokine receptors to NF-κB activation.

TRAF family members are prototypically composed of an N-terminal regulatory domain and a conserved C-terminal TRAF domain (Rothe et al., supra, 1994). The TRAF domain mediates oligomerization, interaction with the receptor, and interaction with various signaling effectors while the N-terminal domain contains a RING finger and several zinc fingers which appears to regulate the activity of its associated signaling molecules (reviewed in Arche, et al., Genes Dev., 12:2821–2830, 1998). Several TRAF family members associate with and activate apoptosis signal-regulating kinase 1 (ASK1) which activates c-Jun N-terminal kinase (JNK) (Nishitoh et al., Mol. Cell, 2:389-395, 1998), and also NF-κB inducing kinase (NIK) which induces NF-κB activation (Malinin et al., Nature, 385:540–544, 1997). Although the TRAF domain alone is sufficient to mediate interaction with these kinases, it is not sufficient to induce their activation. The N-terminal RING and zinc fingers of TRAF proteins are also required to intiate downstream signaling although the precise mechanisms by which these regulatory elements function are not understood (Rothe et al., supra, 1995; Malinin, et al., supra, 1998).

Despite the rapid advancement of knowledge of the effects of TNF-related cytokines on cells, there is still a great amount of information about these factors that remains unknown. Thus, there is a need in the art for identification of elements of the TRANCE signal transduction pathway.

There is a further need in the art for identification of elements of the pathway that are involved in signal transduction of other TNF-related cytokines.

These and other needs in the art are addressed by the present invention.

BRIEF DESCRIPTION OF THE DRAWINGS

FIG. 1. TRANCE activates p44/42 ERK, NF-κB and PKB in osteoclasts and dendritic cells. (A) Mature bone marrow-derived osteoclasts were stimulated for the indicated times with recombinant hCD8-TRANCE (TRANCE; 1 μg/ml). Levels of phosphorylated forms of p44/p42 ERK (p44 ERK$^P$ and p42 ERK$^P$), IκBα (IκB-α$^P$) and PKB (PKB$^P$) in whole cell extracts were determined using phospho-peptide-specific antibodies as indicated in the figure. The membranes were stripped and incubated with antibodies against the p44/p42 ERK, IκB-α, and PKB as indicated to confirm that similar amounts of whole cell extracts were analyzed. Note the decrease of IκB-α after 10 min of treatment due to its degradation. (B) as in (A) except the use of mature bone marrow-derived dendritic cells instead of osteoclasts.

FIG. 5. Ligand dependant recruitment of endogenous TRAF6 and c-Src proteins to the TRANCE-R signaling complex. (A) Dendritic cells were stimulated with TRANCE (1 μg/ml) for the indicated times, lysed, and c-Src was immunoprecipitated from the extracts (400 μg total protein), using an anti-c-Src-specific monoclonal antibody (327). PTK activity of the c-Src immunoprecipitates was measured by in vitro kinase assays using SAM68 as a PTK substrate. The degree of SAM68 phosphorylation (SAM68$^P$) was determined by Western blot analysis using a phospho-tyrosine specific antibody (4G10) followed by densitometry. (B) Dendritic cells (3×10$^7$) were treated with TRANCE (1 μg/ml) for 5 minutes or left untreated (0 minutes). The cells were harvested and the endogenous TRANCE-R was immunoprecipitated from the extracts (2 mg of total protein), using an affinity-purified polyclonal antibody specific for TRANCE-R (α-TRANCE-R). One-third of each immunoprecipitate was subjected to in vitro kinase assays using SAM68. The degree of SAM68 phosphorylation (SAM68$^P$) was determined as in (A). The presence of endogenous TRAF6 or c-Src in the remaining α-TRANCE-R immunoprecipitates (IP) were analyzed by Western blotting using TRAF6 (H-274) and c-Src specific antibodies (N16), respectively, as indicated.

DETAILED DESCRIPTION OF THE INVENTION

Figure 2A:
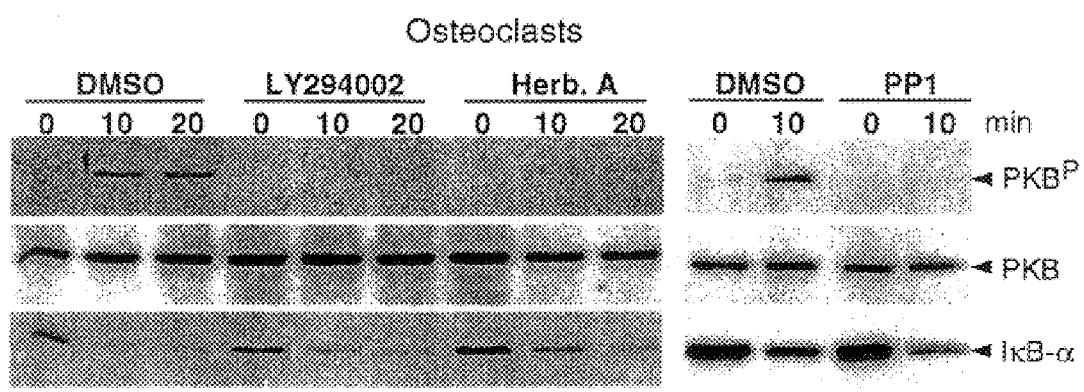
FIG. 2. TRANCE-induced PKB activation in osteoclasts and dendritic cells is blocked by inhibitors of PI3-kinase, tyrosine kinases and Src family kinases. (A) Osteoclasts were serum starved and then pretreated for 90 min with LY294002 (10 μM), Herbimycin A (Herb. A; 10 μM), and PP1 (10 μM) inhibitors which are specific for PI3-kinase, PTKs, and Src-family kinases, respectively, were stimulated for indicated times with TRANCE (1 μg/ml). Levels of phosphorylated p44/p42 ERK, PKB, and IκB-α were determined as described in FIG. 1. Cells pretreated with vehicle (DMSO) were used as a negative control. (B) as in (A) except the use of mature bone marrow-derived dendritic cells.

TRANCE, a TNF family member and its receptor, TRANCE-R/RANK, regulate the activation and survival of mature dendritic cells and osteoclasts. The present invention is based, in part, on the observation that in these cells, TRANCE activates the anti-apoptotic serine/threonine kinase, Akt/protein kinase B (PKB), and that Akt/PKB activation depends on a mechanism involving Src-family kinases and PI3-kinase. Co-expression experiments also demonstrate that TRANCE-R associates with and activates c-Src through TRAF6 by showing that (i) c-Src associates with regions of the TRANCE-R that interact with TRAF6 but not other TRAF proteins, that (ii) a dominant negative form of TRAF6 blocks TRANCE-R-associated Src-tyrosine kinase activity, and that (iii) TRAF6 directly associates with c-Src. In dendritic cells, stimulation with TRANCE resulted in the recruitment of endogenous TRAF6 and c-Src to the TRANCE-R signaling complex. In addition, TRAF6-mediated c-Src-activation requires both the N-terminal regulatory elements and the TRAF domain of TRAF6. These results demonstrate that TRANCE-R engages TRAF6, c-Src and PI3-kinase, consequently resulting in PKB activation. These observations also suggest that TRAF6 links TNF receptor family members and other cytokine receptors to Src-kinase-mediated signaling cascades.

As used herein, the term "TRANCE" refers to a protein belonging to the TNF superfamily, as described in co-owned co-pending U.S. patent application Ser. No. 09/210,115, filed Dec. 11, 1998, and corresponding International patent application No. PCT/US98/26486. This protein has also been described in U.S. Pat. No. 5,843,678 and International Patent Publication No. WO 98/28426. This protein has also been described in the Background of the Invention. Accordingly, as described in these references, TRANCE includes recombinant and natural proteins; soluble or membrane bound forms of the protein; and truncated or derivative forms of the protein. TRANCE can be obtained from human or non-human animals, and preferably is either human TRANCE or TRANCE corresponding to the species in which testing is to occur. In specific embodiments, TRANCE can be murine TRANCE (see, e.g., PCT/US98/26486).

Other TNF family members include interleukin (IL)-1α, CD40 ligand, 9CD40L, CD30L, CD27L, OX40L, p75 nerve growth factor, LT-α, LT-β, FasL, 4-1BBL, and TRAIL/APO-2L.

The term TRANCE receptor (TRANCE-R) refers to the tumor necrosis family receptor (TNFR) for which TRANCE is a ligand (see the discussion in the Background of the Invention). TRANCE-R is also referred to as RANK (receptor activator of NF-κB) (WO 98/28426). A soluble, decoy TRANCE receptor is termed osteoprotegerin (Yasuda, et al., supra, 1998; Simonet et al., supra, 1997; see U.S. Pat. No. 5,843,678). TRANCE-R can be found endogenously on a number of cells, particularly dendritic cells, but also macrophages, osteoclasts and osteoclast precursors, and related cells. Alternatively, a cell transduced with a vector encoding TRANCE-R can express the functional receptor. Indeed, as discussed below, it is possible to reconstitute TRANCE activity in a cell by modifying the cell to express TRANCE-R (in conjunction with elements of the TRANCE or TNFR signal transduction pathway, as discussed below).

Other TNFR family members (besides TNF receptor) include, but are not limited to, interleukin (IL)-1α receptor, CD40, CD30, CD27, OX 40, p75 nerve growth factor receptor, LT receptor, Fas, 4-1BB, and TRAIL/APO-2.

The term "signal transduction pathway" as used in this invention refers to the intracellular mechanism by which TRANCE (or another TNF-related protein) induces an alteration of cell function or activity, e.g., osteoclast or dendritic cell survival. A key feature of the signal transduction pathway dissected herein is the association of TRAF6 and c-Src with the TRANCE-R (or other TNFR family member), resulting in further signal transduction, including activation of ATK/PKB.

The term "element of a signal transduction pathway" refers to a signal transduction factor that is activated as a result of TRANCE binding to the TRANCE-R. In accordance with the present invention, elements of the TRANCE signal transduction pathway include TRAF6, c-Src (and other src-family proteins that interact with TRAF6, such as Fyn), c-Cb1, ERK, IκB-α, NF-κB, PIK3, and ATK/PKB. A "signal" in such a pathway can refer to activation of an element (or factor) in the pathway. For example, activation of c-Src, c-Cb1, PIK3, or ATK/PKB is a signal of a TRANCE-induced (or other TNF-related protein-induced) signal transduction pathway. Generally, activation of one of these factors involves phosphorylation. In particular, a significant advance of the invention is the discovery that ATK/PKB is regulated by a TNF-related molecule; this had never been observed before. Another important and unexpected discovery of the invention is the key role played by c-Src and src family members (notably Fyn) AKT/PKB activation induced by TNF-related cytokines.

"TRANCE-induced signalling" and "TRANCE-induced signal transduction" refer to the cascade of cellular signals that result from TRANCE binding to a cell that expresses a TRANCE receptor. Alternative methods for inducing this signal transduction include using an agonistic antibody (antibody that binds TRANCE-R and induces receptor aggregation), and overexpression of TRAF6 to activate c-Src (as exemplified infra). Preferably a monoclonal antibody is used as an agonist antibody. This pathway includes association of TRAF6, C-Src, and c-Cb1 with the TRANCE receptor, which leads to PIK3 activation. This, in turn, leads to AKT/PKB activation. AKT is an anti-apoptotic molecule. Expression of this factor leads, inter alia, to survival of osteoclasts. Thus, in a specific embodiment, TRANCE-induced signal transduction leads to AKT-mediated osteoclast survival.

Cells for use in accordance with the invention express a functional TRANCE-R, or another TNFR family member that interacts with TRAF6 and c-Src. Cells that express TRANCE-R endogenously include dendritic cells, macrophages, osteoclasts, and osteoclast precursors. The term "osteoclast precursor" includes macrophages or tumor cells that can commit to differentiate into osteoclasts. In a specific embodiment, RAW 267.4 tumor cells are osteoclast precursors. Alternatively, as mentioned above, cells can be generated using recombinant technology to express TRANCE-R, preferably in conjunction with TRAF6 and a src family member.

The term "inhibitor" is used herein to refer to a compound that can block signalling in the signal transduction pathway described herein. Such an inhibitor may block the pathway at any point, from blocking binding of ligand to receptor to blocking function of antiapoptotic factors that promote cell, such as osteoclast and dendritic cell, survival. Preferably, an inhibitor discovered in accordance with the invention is specific for signals of TRANCE-induced signalling.

The term "agonist" is used herein to refer to a compound that can induce signalling in the signal transduction pathway described herein. Such an inducer may induce the pathway at any point, from mimicking binding of cytokine to a TNFR family member to inducing activation of AKT/PKB. Preferably an agonist discovered in accordance with the invention is specific for signals of TRANCE-induced signalling.

"Screening" refers to a process of testing one or a plurality of compounds (including a library of compounds) for some activity. A "screen" is a test system for screening. Screens can be primary, i.e., an initial selection process, or secondary, e.g., to confirm that a compound selected in a primary screen (such as a binding assay) functions as desired (such as in a signal transduction assay). Screening permits the more rapid elimination of irrelevant or nonfunctional compounds, and thus selection of more relevant compounds for further testing and development. "High throughput screening" involves the automation and robotization of screening systems to rapidly screen a large number of compounds for a desired activity.

As used herein, the term "isolated" means that the referenced material is removed from the environment in which it is normally found. Thus, an isolated biological material can be free of cellular components, i.e., components of the cells in which the material is found or produced. In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined to non-regulatory, non-coding regions, or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" as used herein refers to material that has been isolated under conditions that reduce or eliminate the presence of unrelated materials, i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

Methods for purification are well-known in the art. For example, nucleic acids can be purified by precipitation, chromatography (including preparative solid phase chromatography, oligonucleotide hybridization, and triple helix chromatography), ultracentrifugation, and other means. Polypeptides and proteins can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction, and countercurrent distribution. For some purposes, it is preferable to produce the polypeptide in a recombinant system in which the protein contains an additional sequence tag that facilitates purification, such as, but not limited to, a polyhistidine sequence, or a sequence that specifically binds to an antibody, such as FLAG and GST. The polypeptide can then be purified from a crude lysate of the host cell by chromatography on an appropriate solid-phase matrix. Alternatively, antibodies produced against the protein or against peptides derived therefrom can be used as purification reagents. Cells can be purified by various techniques, including centrifugation, matrix separation (e.g., nylon wool separation), panning and other immunoselection techniques, depletion (e.g., complement depletion of contaminating cells), and cell sorting (e.g., fluorescence activated cell sorting (FACS)). Other purification methods are possible. A purified material may contain less than about 50%, preferably less than about 75%, and most preferably less than about 90%, of the cellular components with which it was originally associated. The "substantially pure" indicates the highest degree of purity which can be achieved using conventional purification techniques known in the art.

In a specific embodiment, the term "about" or "approximately" means within 20%, preferably within 10%, and more preferably within 5% of a given value or range. Alternatively, particularly in biology, the term "about" can mean within an order of magnitude of a given value, and preferably within one-half an order of magnitude of the value.

Vectors

A wide variety of host/expression vector combinations may be employed in expressing DNA sequences encoding ATK/PBK, other second messenger proteins involved in TRANCE signaling, or inhibitors of ATK/PBK, such as antisense nucleic acids or anti-ATK/PKB intracellular antibodies. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., Gene 67:31–40, 1988), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

A vector can be introduced in vivo in a non-viral vector, e.g., by lipofection, with other transfection facilitating agents (peptides, polymers, etc.), or as naked DNA. Synthetic cationic lipids can be used to prepare liposomes for in vivo transfection, with targeting in some instances (Felgner, et. al., Proc. Natl. Acad. Sci. U.S.A. 84:7413–7417, 1987; Felgner and Ringold, Science 337:387–388, 1989; see Mackey, et al., Proc. Natl. Acad. Sci. U.S.A. 85:8027–8031, 1988; Ulmer et al., Science 259:1745–1748, 1993). Useful lipid compounds and compositions for transfer of nucleic acids are described in International Patent Publications WO95/18863 and WO96/17823, and in U.S. Pat. No. 5,459,127. Other molecules are also useful for facilitating transfection of a nucleic acid in vivo, such as a cationic oligopeptide (e.g., International Patent Publication WO95/21931), peptides derived from DNA binding proteins (e.g., International Patent Publication WO96/25508), or a cationic polymer (e.g., International Patent Publication WO95/21931). Recently, a relatively low voltage, high efficiency in vivo DNA transfer technique, termed electrotransfer, has been described (Mir et al., C.P. Acad. Sci., 321:893, 1998; WO 99/01157; WO 99/01158; WO 99/01175). DNA vectors for gene therapy can be introduced into the desired host cells by methods known in the art, e.g., electroporation, microinjection, cell fusion, DEAE dextran, calcium phosphate precipitation, use of a gene gun (ballistic transfection), or use of a DNA vector transporter (see, e.g., Wu et al., J. Biol. Chem. 267:963–967, 1992; Wu and Wu, J. Biol. Chem. 263:14621–14624, 1988; Hartmut et al., Canadian Patent Application No. 2,012,311, filed Mar. 15, 1990; Williams et al., Proc. Natl. Acad. Sci. USA 88:2726–2730, 1991). Receptor-mediated DNA delivery approaches can also be used (Curiel et al., Hum. Gene Ther. 3:147–154, 1992; Wu and Wu, J. Biol. Chem. 262:4429–4432, 1987). U.S. Pat. Nos. 5,580,859 and 5,589,466 disclose delivery of exogenous DNA sequences, free of transfection facilitating agents, in a mammal.

Also useful are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional protein or polypeptide (as set forth above) can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures are DNA-based vectors and retroviral vectors. Methods for constructing and using viral vectors are known in the art (see, e.g., Miller and Rosman, BioTechniques, 7:980–990, 1992). Preferably, the viral vectors are replication defective, that is, they are unable to replicate autonomously in the target cell. In general, the genome of the replication defective viral vectors which are used within the scope of the present invention lack at least one region which is necessary for the replication of the virus in the infected cell. These regions can either be eliminated (in whole or in part), be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 2:320–330, 1991), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al., (J. Clin. Invest. 90:626–630, 1992; see also La Salle et al., Science 259:988–990, 1993); and a defective adeno-associated virus vector (Samulski et al., J. Virol. 61:3096–3101, 1987; Samulski et al., J. Virol. 63:3822–3828, 1989; Lebkowski et al., Mol. Cell. Biol. 8:3988–3996, 1988).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, for in vivo administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors (see, e.g., Wilson, Nature Medicine, 1995). In that regard, it is advantageous to employ a viral vector that is engineered to express a minimal number of antigens.

TRANCE and TNF-related Cytokine Responsive Cells

As noted above, certain cells, such as dendritic cells, macrophages, osteoclast precursors, and osteoclasts endogenously express TRANCE-R and respond to TRANCE. The responsiveness of dendritic cells and osteoclasts is exemplified below. Such cells can be stimulated, e.g., to activate them or induce differentiation, as described in the Example. The invention contemplates using in vitro differentiated cells, cell lines (such as the tumor cell line RAW267), or primary cells.

Alternatively, the present invention provides for generation of a TRANCE or other TNF-related cytokine responsive cell using genetic engineering. Vectors for expression of components of the TRANCE signal transduction pathway are available, e.g., as described in the Example, infra. At the very least, a genetically engineered TRANCE responsive cell is modified to express a TRANCE-R or another TNF-related cytokine receptor (TNFR family receptor). It may also be modified to express TRAF6 or c-Src, or both, depending on whether the cell endogenously expresses these factors. If necessary, the cell can be engineered to express other downstream factors, such as c-Cb1, NF-κB, IκB, PI3K, etc.

Thus, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. ÊPerbal, *A Practical Guide To Molecular Cloning* (1984); F. M. Ausubel et aL (eds.), *Current Protocols in Molecular Biology,* John Wiley & Sons, Inc. (1994).

Molecular Biology—Definitions

A "nucleic acid molecule" refers to the phosphate ester polymeric form of ribonucleosides (adenosine, guanosine, uridine or cytidine; "RNA molecules") or deoxyribonucleotides (deoxy adenosine, deoxyguanosine, deoxythymidine, or deoxycytidine; "DNA molecules"). A "recombinant DNA molecule" is a DNA molecule that has undergone a molecular biological manipulation.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" or "operatively associated with" of transcriptional and translational control sequences in a cell when RNA polymerase transcribes the coding sequence into mRNA, which is then trans-RNA spliced (if it contains introns) and translated into the protein encoded by the coding sequence.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes.

The term "expression system" means a host cell and compatible vector under suitable conditions, e.g. for the expression of a protein coded for by foreign DNA carried by the vector and introduced to the host cell. Expression systems include mammalian host cells and vectors. Suitable cells include C12 cells, CHO cells, HeLa cells, 293 and 293T (human kidney cells), mouse primary myoblasts, and NIH 3T3 cells.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared. Finally, for purposes of the invention, a functional-conservative variant includes a truncated or form of the protein that performs its function, such as truncated TRANCE-R, TRAF6, and c-Src described in the Examples, infra.

Similarly, in a particular embodiment, two amino acid sequences are "substantially homologous" or "substantially similar" when greater than 80% of the amino acids are identical, or greater than about 90% are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–9.51). For hybridization with shorter nucleic acids, i.e., oligonucleotides, the position of mismatches becomes more important, and the length of the oligonucleotide determines its specificity (see Sambrook et al., supra, 11.7–11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization and/or washing conditions at 68° C. in 0.2× SSC, at 42° C. in 50% formamide, 4×SSC, or under conditions that afford levels of hybridization equivalent to those observed under either of these two conditions.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, MRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of Ozz, or to detect the presence of nucleic acids encoding Ozz. In a further embodiment, an oligonucleotide of the invention can form a triple helix with a Ozz DNA molecule. Generally, oligonucleotides are prepared synthetically, preferably on a nucleic acid synthesizer. Accordingly, oligonucleotides can be prepared with non-naturally occurring phosphoester analog bonds, such as thioester bonds, etc.

The present invention provides antisense nucleic acids (including ribozymes), which may be used to inhibit expression of Ozz of the invention, particularly to suppress Ozz regulation of β-catenin. An "antisense nucleic acid" is a single stranded nucleic acid molecule which, on hybridizing under cytoplasmic conditions with complementary bases in an RNA or DNA molecule, inhibits the latter's role. If the RNA is a messenger RNA transcript, the antisense nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. Nos. 5,814,500; 5,811,234), or alternatively they can be prepared synthetically (e.g., U.S. Pat. No. 5,780,607).

Specific non-limiting examples of synthetic oligonucleotides envisioned for this invention include oligonucleotides that contain phosphorothioates, phosphotriesters, methyl phosphonates, short chain alkyl, or cycloalkl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—$PO_2$—O—$CH_2$). U.S. Pat. No. 5,677,437 describes heteroaromatic olignucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substitued silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

Screening Assays

As exemplified in the Example, infra, the present invention further provides various screening assays for TNF-related cytokine, and particularly TRANCE, induced activation. The assays of the invention are particularly advantageous by permitting rapid evaluation of cellular response. Biological assays, which depend on cell growth, survival, or some other response require substantial amounts of time and resources to evaluate. By detecting individual signals in the TRANCE-induced signal transduction pathway, the present invention short-circuits the more tedious and time consuming biological assays. Furthermore, the signal transduction assays can often be performed with very small amounts of material.

In general, a screening assay of the invention makes use of the cells described above, TRANCE (e.g., in soluble form) or another TNF-related cytokine, and a candidate compound for testing.

The present invention contemplates screens for small molecule compounds, including ligand analogs and mimics, as well as screens for natural compounds that bind to and agonize or antagonize TRANCE signal transduction in vivo. Such agonists or antagonists may, for example, interfere in the phosphorylation or dephosphorylation of signal transduction proteins. For example, natural products libraries can be screened using assays of the invention for such molecules. As used herein, the term "compound" refers to any molecule or complex of more than one molecule that affects TRANCE signal transduction resulting in AKT/PKB activation. The present invention contemplates screens for synthetic small molecule agents, chemical compounds, chemical complexes, and salts thereof as well as screens for natural products, such as plant extracts or materials obtained from fermentation broths. Other molecules that can be identified using the screens of the invention include proteins and peptide fragments, peptides, nucleic acids and oligonucleotides (particularly triple-helix-forming oligonucleotides), carbohydrates, phospholipids and other lipid derivatives, steroids and steroid derivatives, prostaglandins and related arachadonic acid derivatives, etc.

One approach to identifying such compounds uses recombinant bacteriophage to produce large libraries. Using the "phage method" (Scott and Smith, Science 249:386–390, 1990; Cwirla, et al., Proc. Natl. Acad. Sci., 87:6378–6382, 1990; Devlin et al., Science, 49:404–406, 1990), very large libraries can be constructed ($10^6$–$10^8$ chemical entities). A second approach uses primarily chemical methods, of which the Geysen method (Geysen et al., Molecular Immunology 23:709–715, 1986; Geysen et al. J. Immunologic Method 102:259–274, 1987; and the method of Fodor et al. (Science 251:767–773, 1991) are examples. Furka et al. (14th International Congress of Biochemistry, Volume #5, Abstract FR:013, 1988; Furka, Int. J. Peptide Protein Res. 37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic combinatorial libraries (Needels et al., Proc. Natl. Acad. Sci. USA 90:10700–4, 1993; Ohlmeyer et al., Proc. Natl. Acad. Sci. USA 90:10922–10926, 1993; Lam et al., International Patent Publication No. WO 92/00252; Kocis et al., International Patent Publication No. WO 9428028) and the like can be used to screen for compounds according to the present invention.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK.), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., Tib Tech, 14:60, 1996).

Methods for Detecting Signals

The present invention provides numerous methods for detecting signals, including but not limited to directly detecting phosphorylation of proteins using radioactive phosphorous compounds, indirectly detecting phosphorylation with antibodies specific for phosphorylated epitopes, or detecting signals from activated signal transduction proteins, such as gene expression. Preferably, gene expression is detected using a reporter gene assay. Alternatively, a downstream element of a signal transduction pathway can be modified to have reporter activity. Reporter genes for use in the invention encode detectable proteins, including, but are by no means limited to, chloramphenicol transferase (CAT), β-galactosidase (β-gal), luciferase, green fluorescent protein, alkaline phosphatase, and other genes that can be detected, e.g., immunologically (by antibody assay).

The intracellular signaling molecules that are activated in response to the binding of TRANCE to its receptor include Cbl, c-Src, TRAF-6, PKB/AKT, and PI3-kinase. Binding of TRANCE to TRANCE-R induces the formation of a cytoplasmic quaternary complex. This complex consists of the receptor itself, along with TRAF6, Cbl and c-Src. The formation of this complex ultimately results in the activation of PI3-kinase and PKB/AKT, which mediate the anti-apopotic effects of TRANCE. The activation of the downstream intermediates can be utilized to measure activation of the TRANCE-R and the anti-apopotic effects of TRANCE.

The proto-oncogene Cbl is an adaptor protein which is activated by tyrosine phosphorylation. Steady state levels of Cbl protein can be detected by Western blotting as described by Wunderlich et al., Eur. J. Immunol., 29: 1068–75, 1999; and Lavagna-Sevenier et al., Leukemia, 12: 301–10, 1998. While the phosphorylated, activated form of Cbl can determined as described by Howlett et al., Biochem. Biophys. Res. Commun., 257: 129–38, 1999. To determine whether Cbl exists in a complex with other intracellular signaling molecules, an antibody to Cbl can be used to immunoprecipitate associated proteins as described by Lavagna-Sevenier et al., supra; and Erdriech-Epstein et al, J. Leukoc. Biol., 65: 523–34, 1999.

C-Src is normally inhibited by phosphorylation on the carboxy terminus of the protein. De-phosphorylation and activation of c-Src allows it to function as a kinase molecule and phosphorylate other proteins. C-Src has been demonstrated to interact with the TRANCE-R in a complex that consists of the receptor, c-Src, Cbl, and TRAF6. The presence of c-Src in this complex can be determined through immunoprecipitation with antibodies to Cbl followed by Western blotting as described by Danilovich and Leonard, J. Leukoc. Biol., 65: 345–8, 1999; and Lutz et al., Biochem. Biophys. Res. Commun. 243: 503–8, 1998. Additionally, the phosphorylation state of c-Src can be determined through the use of activation-state-specific antibodies (U.S. Pat. No. 5,599,681).

TRAF6 is a member of the TNF receptor-associated factor family. The binding of TRAF6 to TRANCE-R can be analyzed by co-immunoprecipitation and Western blotting using antibodies to TRAF6 and the TRANCE-R as described by Khursigara et al, J. Biol. Chem., 274: 2597–600, 1999; Wong et al., J. Biol. Chem., 273: 28355–9, 1998; and Cao et al., Nature, 383: 443–6, 1996.

The phosphorylation induced activation of AKT may also be used to examine TRANCE signaling. This activation can be examined as described by Bao et al., Blood, 93: 3757–3773, 1999; and Danilovich and Leonard, J. Leukoc. Biol., 65: 345–8, 1999. The cellular localization of PKB/AKT in both fibroblasts and epithelial cells is specific and is disrupted by PI3-kinase inhibitory drugs (Watton and Downward, Curr. Biol., 22: 433–6, 1999). Both PKB and a PKB/GFP fusion protein demonstrated altered sites of localization in the presence of inhibitors of PI3-kinase. Should a similar fusion protein show a specific pattern of localization in TRANCE-treated cells, it would provide a convenient method to evaluate the TRANCE signal transduction pathway.

The activation of PI3-kinase can be determined as described by Kanagasundaram et al., Mol.Cell Biol., 19:4079–92; and Bao et al., Blood, 93: 3757–3773, 1999. The activity of PI3-kinase can be tested directly by utilizing the PI3-kinase inhibitory drugs wotmannin and LY-294002 as described by Watton and Downward, supra; and de Luca et al., Am. J. Physiol., 276: H1520–6, 1999.

AKT Activation

The present discovery has, as a corollary, the discovery that AKT mediates osteoclast survival. Thus, the invention advantageously provides for modulating osteoclast activity by inhibiting or activating AKT/PKB.

For example, inhibiting osteoclast survival can be effected by directly blocking AKT activation. It should be noted that AKT activation can be blocked directly, e.g., by blocking expression of AKT. Alternatively, upstream steps in the AKT activation path could be inhibited. However, since it is already known that TRANCE promotes osteoclast survival (although it was not known that TRANCE induces AKT activation, which appears to be the mechanism for osteoclast survival), inhibition of AKT activation to inhibit osteoclast survival does not include inhibition of TRANCE.

Direct blocking of AKT can be accomplished by using anti-AKT triple-helix oligonucleotides, anti-sense nucleic acids, or ribozymes to block AKT expression. Alternatively, expression of AKT can be blocked with an anti-AKT intracellular antibody (intrabody), e.g., single chain Fv antibodies (see generally, Chen, Mol. Med. Today, 3:160–167, 1997; Spitz et al., Anticancer Res., 16:3415–3422, 1996; Indolfi et al., Nat. Med., 2:634–635, 1996; Kijima et al., Pharmacol. Ther., 68:247–267, 1995).

Alternatively, inhibition of upstream signal transduction mechanisms can block AKT activation. For example, inhibition of Src, Cbl, or PIK3 activation may block AKT activation. Such inhibitors include various kinase inhibitors. Preferably, such inhibitors are specific for the signal transduction factors in the AKT activation pathway.

AKT/PKB activity can be increased by increasing the level of expression of this factor. Gene transfer, or gene therapy, provides one strategy for increasing expression of AKT/PKB. A vector as described above, encoding AKT/PKB, can be introduced into target cells to express the polypeptide.

Alternatively, activation of the TRANCE signal transduction pathway will be expected to activate AKT/PKB. Such activation can be effected by introducing high levels of one or more of TRANCE-R, TRAF6, and c-Src, e.g., as described in the Example. Such factors can be introduced using the vectors described above.

EXAMPLES

The present invention will be better understood by reference to the following examples, which are provided by way of exemplification and are not intended to limit the invention.

Example 1
TRANCE Induced PKB Activation Involving TRAF6 and c-Src

The present example shows that TRANCE activates PKB, a serine/threonine kinase that potentiates cell survival by phosphorylating and inhibiting several effectors of apoptosis. Examination of the mechanism activating PKB by TRANCE revealed the involvement of TRAF6, Src-family kinases and PI3-kinase. TRAF6 and c-Src assemble at the TRANCE-R complex upon ligand engagement. TRAF6 directly regulates c-Src kinase activity and is essential for the Src-dependent PTK activity associated with TRANCE-R. Furthermore, TRAF6, in addition to TRAF1 and TRAF3, directly associates with Src-family kinases suggesting that several families of cytokine receptors can cross-talk to Src-family kinase-mediated signaling pathways through TRAF adapter proteins. These results reveal a novel mode of signaling by TRANCE-R, a TNFR family members and other cytokine receptors, and furthers our understanding of how these molecules regulate various cellular responses.

Materials and Methods

Reagents. LY294002, and Herbimycin A were purchased from Calbiochem; PP1 was prepared as described; recombinant CSF-1, TNF and IL-1 were purchased from R&D Systems; E. Coli 055:B5 LPS from Sigma; SAM68, a PTK substrate from Santa Cruz Biotechnology; Bio-Rad protein assay from Bio-Rad; recombinant soluble hCD8-TRANCE (TRANCE) and mCD8-CD40L were purified from insect cells by a baculovirus expression system as described (Wong et al., supra, 1997); [$\gamma$-$^{32}$P]ATP (3,000 Ci/mmol) and the Renaissance immunodetection system were from New England Nuclear and GammaBind G-Sepharose and Protein G-Sepharose from Pharmacia.

Antibodies specific for phospho-p44/42 ERK (Thr202/Tyr204), phospho-I$\kappa$B-$\alpha$ (Ser32), I$\kappa$B-$\alpha$, phospho-PKB (Ser473) and PKB were obtained from New England Biolabs; c-Src (N-16), ERK1 (C-16), ERK2 (C-14), c-Cbl (C-15), Fyn (FYN3), and Hck (N-30) from Santa Cruz Biotechnology; phospho-tyrosine (4G10) from Upstate Biotechnology Inc.; the FLAG-epitope (M2) from Kodak; the HA epitope (12CA5) from Boehinger Mannheim; c-Cbl (17) from Transduction Laboratories. Horseradish peroxidase-conjugated anti-rabbit and anti-mouse antibodies (Santa Cruz Biotechnology or Amersham) were used as secondary antibodies on Western blots. The monoclonal antibody, 327, against c-Src was purified from hybridoma supernatents. Polyclonal antibodies for TRANCE-R were prepared by immunizing female Syrian hamsters (Charles River Labs) and by affinity purifying sera over a Protein A-Sepharose column conjugated to recombinant TRANCE-R protein.

Primary cells and cell lines. Osteoclasts and macrophages were generated from bone marrow precursors as described (Wani, et al., Endocrinology, 140:1927–1635, 1999). In brief, bone marrow cells from tibiae and femur of 4–6 week old mice (C57BL/6, Jackson Laboratories) were cultured overnight in media ($\alpha$-MEM, 10% FCS) in the presence of CSF-1 (5 ng/ml). After 24 hours, non-adherent cells were harvested, washed, and further cultured in media with CSF-1 (50 ng/ml) plus TRANCE (10 ng/ml) to develop osteoclasts, or with CSF-1 alone to develop macrophages. Using these conditions, after 4 days of culture, greater than 95 percent of the adherent cells were osteoclasts or macrophages. For experiments described in this study, only adherent cells were used after extensive washing. Mature dendritic cells were generated from bone marrow precursors of 4–6 week old female C57BL/6 mice (C57BL/6, Jackson Laboratories) cultured in media (RPMI1640, 5% FBS) and GM-CSF (1:30 cultured supernatant from the J558 cell line, a gift from Dr. R. M. Steinman, The Rockefeller University) for 8 days as previously described (Inaba, et al., J. Exp. Med., 176:1693–1702, 1992). To generate osteoclasts and dendritic cells from c-Src deficient mice, spleen cells, which contain hematopoietic precursors due to extramedullary hematopoeisis, were substituted for bone marrow cells as previously described (Schwartzberg, et al., Genes Dev., 11:2835–2844, 1997). Mature spleen-derived dendritic cells were isolated from spleens treated with collagenase (40 U/ml; Boehinger Mannheim) and subjected to a Nycodenz centrifugation gradient (14.5%; Nycomed) to obtain low density cells. After allowing them adhere for 2 hours to a tissue culture dish, contaminating floater cells were washed away and mature dendritic cells were obtained by overnight culture.

293 cells and 293T cells (Pear, et al., Proc. Natl. Acad. Sci. U.S.A., 90:8392–8396, 1993) were cultured in DMEM supplemented with 10% fetal bovine serum.

Plasmids. Expression constructs encoding FLAG-tagged wild type TRANCE-R (TR-wt), TRAF5, TRAF6 were described (Wong, et al., supra, 1997). Constructs encoding TRANCE-R deletion mutants (TR-235-559, -235-358, -354-536, -532-635, -ecto: extracellular domain only), which are comprised of a FLAG-tagged TRANCE-R extracellular domain fused to various regions of the cytoplasmic tail (defined by amino acid residues in the TRANCE-R) were described (Wong, et al., supra, 1997). TRAF1, TRAF2, TRAF3, TRAF6(1–289) and TRAF6(289–530) were cloned by PCR into pFLAG-CMV-2. Expression plasmids for c-Src, c-SrcK295M, c-Cbl, c-Fyn and Hck were constructed by introducing the respective coding sequences into pcDNA3.1 (Invitrogen).

Cell stimulation, cell transfection and in vitro assays. In vitro differentiated mature dendritic cells, macrophages and osteoclasts were washed to remove exogenous growth factors, cultured in media with low serum (0.5% FCS, 6 hours), then stimulated by adding various cytokines in the presence or absence of inhibitors for various times as indicated. After stimulation, the cells were washed in ice-cold PBS, and subjected to Western blot analysis or immunoprecipitation as described below.

For transfection, 293 ($5 \times 10^5$ cells/well) and 293T ($3 \times 10^5$ cells/well) cells were cultured on 6-well plates for 24 hours then transfected using either the MBS transfection system (Stratagene) as described by the manufacturer or by $CaPO_4$ precipiation as described (Wong, et al., supra, 1997). In general, the amount of transfected DNA was kept constant at 2 $\mu$g by the addition of vector plasmid. The cells were processed for further analysis 36 hours after transfection.

All cells were harvested and lysed in extraction buffer (20 mM HEPES NaOH (pH 7.4), 150 mM NaCl, 1% Triton X-100, 10% glycerol, 10 mM EDTA, 1 mM $Na_3VO_4$, 1 mM phenylmethylsulfonylfluoride, 1 $\mu$g/ml leupeptin, and 0.1 U of aprotinin per ml) and cleared by centrifugation to obtain whole cell extracts. Protein assays were performed to ensure equal amounts of lysates were used in each sample.

Immunoprecipitations were performed on whole-cell extracts with various antibodies as indicated. Briefly, for each precipitation, 1 $\mu$g of antibody was incubated with 30 $\mu$l of GammaBind G-Sepharose or Protein G-sepharose on a rocker table (4° C., 1 hour). The Sepharose beads, bound to antibody, were transferred to 400 $\mu$g of whole-cell extracts (adjusted to 1 mg of total protein/ml) and incubated for another 2 hours, then washed four times with extraction buffer. The immunoprecipitates were then subjected to sodium dodecyl sulfate-polyacrylamide gel electrophoresis (SDS-PAGE) and Western blotting.

Figure 3A:
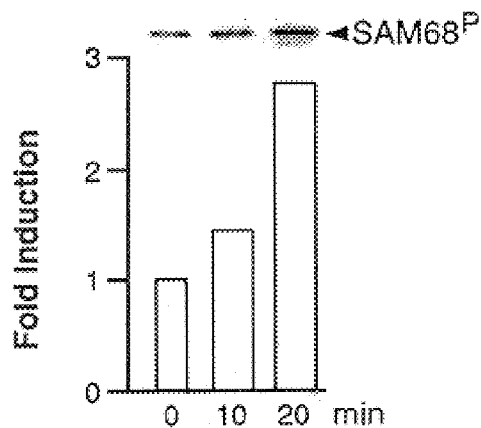
FIG. 3. c-Src is required for TRANCE-induced PKB activation and osteoclast survival. (A) c-Src was immunoprecipitated from osteoclasts, dendritic cells and macrophages stimulated with TRANCE (1 μg/ml) for the indicated times using an anti-c-Src-specific monoclonal antibody (327). PTK activity of the c-Src immunprecipitates were measured in vitro using SAM68, a PTK specific substrate. The degree of SAM68 phosphorylation was determined by Western blot analysis using an anti-phospho-tyrosine antibody (4G10) and densitometry. Note that c-Src kinase activity was not detectable in TRANCE-treated macrophages most likely due to low levels of c-Src in these cells (Lacey, et al., supra, 1998). (B) Osteoclasts derived from wild type and c-Src deficient mice were stimulated with TRANCE (5 μg/ml) for 10 min and the levels of phosphorylated PKB (PKB$^P$), total PKB, and total IκBα were determined as in FIG. 1. (C) Osteoclasts from wild-type (open bars) and c-Src deficient (solid bars) mice were washed and then cultured for an additional 24 hours in media alone (Medium) or in media with TRANCE (5 μg/ml) or CSF-1 (10 ng/ml). TRAP solution assays were performed and percent survival calculated. The experiment was performed in triplicate and the mean values with positive standard deviations are shown. (D) Osteoclasts were differentiated with TRANCE (100 ng/ml) plus CSF-1 (50 ng/ml) in the absence or presence of increasing doses (200 nM and 800 nM) of the PI3-kinase inhibitor LY294002. Osteoclasts were detected by TRAP solution assays. The experiment was performed in triplicate and the mean values with positive standard deviations are shown. (E) Mature osteoclasts were washed extensively and then cultured for an additional 24 hr in media without (−) or with TRANCE (5 μg/ml; +) in the absence or presence of increasing doses (200 nM and 800 nM) of LY294002. TRAP solution assays were performed and percent survival was as described in Experimental Procedures. The experiment was performed in triplicate and the mean values with positive standard deviations are shown.
Figure 4A:
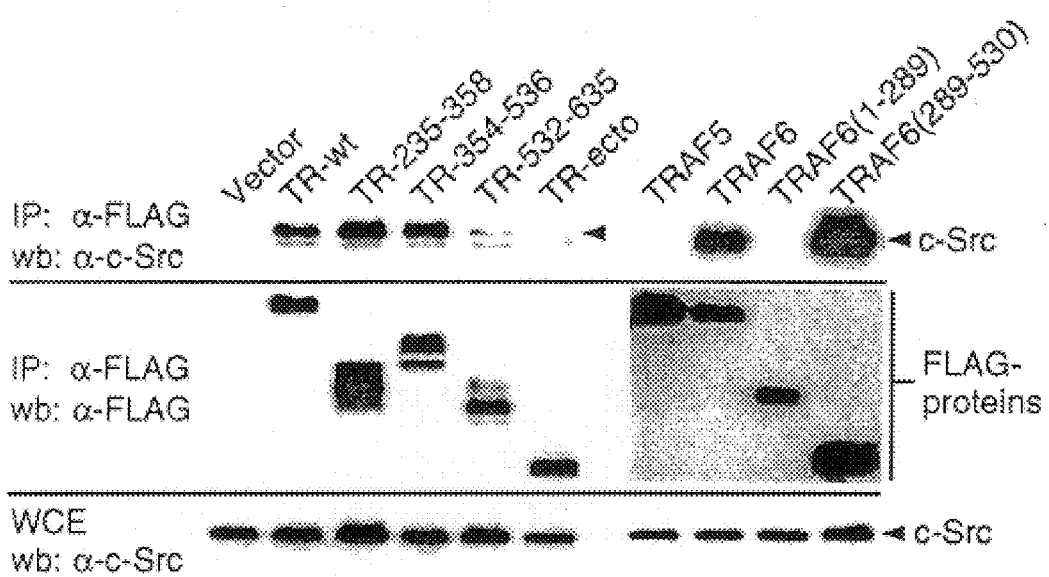
FIG. 4. TRANCE-R interacts with and activates c-Src via TRAF6. (A) 293T cells were co-transfected with pcDNA3.1/c-Src (0.5 μg) together with pFLAG1 (vector, 0.5 μg) or expression constructs encoding for the various FLAG-tagged TRANCE-R proteins (numbers correspond to the amino acids of the intracellular portion of TRANCE-R (TR); 0.5 μg), TRAF5, TRAF6, or TRAF6 deletion mutatnts (numbers correspond to the amino acids of TRAF6 as indicated). 36 hours after transfection, the cells were harvested, lysed and the various FLAG-tagged TR and TRAF proteins were immunoprecipitated from the whole cell extracts (WCE; 400 μg total protein), using the FLAG-specific antibody (α-FLAG). Immunoprecipitates (IP) and WCE were analyzed by Western blotting (wb) to detect c-Src or various FLAG-tagged TR and TRAF proteins as indicated. (B) 293T cells were transfected with pFLAG1 (Vector; 0.5 μg) or expression constructs (0.5 μg each) for the various FLAG-tagged TRANCE-R (TR) proteins. 36 hours after transfection, the cells were harvested and whole-cell extracts (WCE) were prepared. The various FLAG-tagged TR proteins were immunoprecipitated from the extracts (400 μg total protein) using the FLAG-specific antibody (α-FLAG) and subjected to in vitro kinase assays with SAM68. Tyrosine phosphorylated SAM68 (SAM68) was detected by Western blot analysis using a phospho-tyrosine specific antibody (4G10). To control for the expression of various FLAG-tagged TRANCE-R proteins, the western blots were stripped and reprobed with an antibody specific for FLAG (α-FLAG). (C) A summary diagram describing the various TR constructs used in (A) and (B) and their respective ability to associate with TRAF proteins (Wong et al., supra, 1998; Galibert et al., supra, 1998; Darnay et al., supra, 1999) and c-Src, and endogenous PTK activity. (D) In vitro kinase assays using SAM68 as a substrate were performed as in (B) except that the FLAG-tagged TRANCE-R (TR; 0.5 μg) protein was coexpressed with either kinase-inactive c-Src (c-Src(K295M); 1.5 μg) or dominant negative HA-tagged TRAF6 (HA-TRAF6(289–530); 1.5 μg). Controls for the expression of FLAG-TR-wt, FLAG-TR-ecto in the a-FLAG immunoprecipitates, and for c-Src(K295M) and HA-tagged TRAF(289–530) in whole-cell extracts are shown. (E) 293 cells were co-transfected with combinations of expression constructs for FLAG-TRAF6 (0.2 μg), FLAG-TRAF6(289–530) (150 and 600 ng), c-Src(K295M) (50 and 150 ng), c-Src (10 ng), and c-Cb1 (200 ng) as indicated. 36 hours after transfection, the cells were harvested, lysed and c-Cb1 was immunoprecipitated form whole cell extracts (400 μg total protein). Immunoprecipitates and WCE were analyzed by Western blotting for tyrosine phosphorylated c-Cb1 (c-Cb1), c-Cb1, c-Src, or TRAF6 molecules as indicated. Western blot analysis for c-Src detected both wild-type c-Src and c-Src(K295M).
Figure 4B:
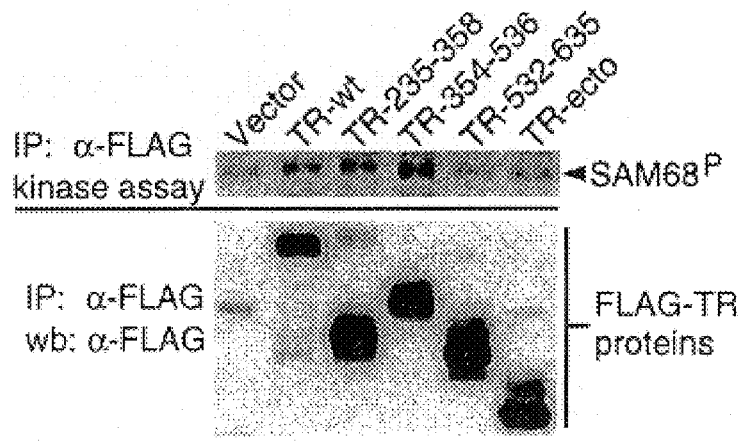
Figures 4C, 4D:
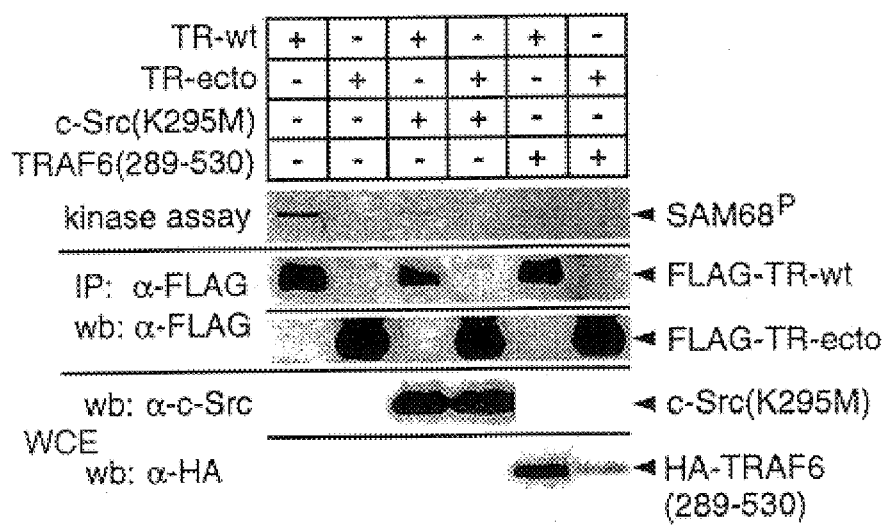

For the in vitro kinase-assays in FIGS. 3A, 4D, and 5B the beads were washed twice with extraction buffer and three times with kinase buffer (30 mM HEPES.NaOH (pH 7.4), 20 mM $MgCl_2$, 2 mM $MnCl_2$, 1 mM dithiothreitol). The kinase reaction (20 $\mu$l of kinase buffer, 0.5 mg SAM68, 2 mCi ($\gamma$-$^{32}$P)ATP, 10 $\mu$M ATP) was carried out for 30 minutes at 30° C. and then subjected to SDS-PAGE, and Western blotting. Phosphorylation of SAM68 was detected by autoradiography or by probing Western blots with 4G10.

For Western blotting, whole-cell extracts (20 $\mu$g of total protein), immunoprecipitates or kinase reactions were resolved on SDS-PAGE, electro-blotted to PVDF membranes (Immobilon-P, Millipore) according to standard methods (Maniatis, et al., Molecular Cloning: A Laboratory Manual (Cold Spring Harbor Laboratory, New York) 1989), probed with antibodies according to the manufacturer's protocol, and visualized using an immunodetection system. Stripping was performed by incubating the blots in stripping buffer (62.5 mM Tris pH 6.8, 2% SDS, 100 mM $\beta$-mercaptoethanol) for 30 min at 55° C.

Osteoclast survival assays. In vitro differentiated mature osteoclasts were washed 3 times in media then further cultured for 24 hr in media alone (control) or in media with TRANCE (5 $\mu$g/ml) or CSF-1 (10 ng/ml) in the presence or absence of LY294002 as indicated. Absorbance values at 405 nm ($A_{405}$) from tartrate resistant acid phosphatase (TRAP) solution assays of cell lysates (Lum, et al., J. Biol. Chem., 274:13613–13618, 1999) were used to calculate osteoclast survival using the following equation:

Specific cell survival (%)=$(A_{405,\ 24\ hr} - A_{405,\ background}) * 100 / (A_{405,\ 0\ hr} - A_{405,\ background})$ Background absorbance ($A_{405,\ background}$) was determined by measuring the TRAP activity of cell lysins buffer.

Results

TRANCE activates ERK, NF-$\kappa$B and PKB in osteoclasts and dendritic cells. TRANCE regulates cell survival, activation, and the morphology of osteoclasts and dendritic cells, two major cellular targets of TRANCE identified to date. However, the signaling events which mediate these effects are unknown. JNK and NF-$\kappa$B are activated by TRANCE in T cells and in cell lines overexpressing TRANCE-R. However, JNK does not appear to be activated by TRANCE in dendritic cells suggesting that cell type-specific mechanisms regulate signaling initiated by TRANCE-R (Wong, et al., supra, 1997). Therefore, we analyzed several signaling pathways regulated by TRANCE in osteoclasts and dendritic cells. Upon TRANCE treatment, phosphorylated forms of extracellular-signal-regulated kinase (ERK)1 and 2 and I$\kappa$B-$\alpha$ were detected by phosphopeptide-specific antibodies in both osteoclasts (FIG. 1A) and dendritic cells (FIG. 1B). TRANCE also resulted in a decrease of total cellular I$\kappa$B-$\alpha$ beginning at 10 min, coinciding with the peak of I$\kappa$B-$\alpha$ phosphorylation, events required for NF-$\kappa$B activation. ERK phosphorylation was transiently induced after 20 min of TRANCE stimulation. JNK activation as measured by its phosphorylation was not detected in dendritic cells, as previously reported (Wong, et al., supra, 1997), nor in osteoclasts (data not shown). These results indicate that TRANCE induces the activation of ERK and NF-$\kappa$B, but not of JNK in osteoclasts and dendritic cells.

Activation of ERK and NF-$\kappa$B has been implicated in various anti-apoptotic signaling pathways (Xia, et al., Science, 270:1326–1331, 1995; and reviewed in Baichwal, et al., Curr. Biol., 7:R94–96, 1997), raising the possibility that TRANCE may regulate the survival of osteoclasts and dendritic cells via ERK and/or NF-$\kappa$B. Since TRANCE is a potent survival factor in dendritic cells and osteoclasts we attempted dentify other signaling molecules that may regulate anti-apoptotic signals by TRANCE in those cells. One candidate molecule was Akt/protein kinase B (PKB), a serine/threonine kinase activated by an array of growth factors and cytokines, which has been demonstrated to regulate cell survival by phosphorylating and inactivating pro-apoptotic molecules. Although PKB has not been shown to be regulated by TNF-related molecules, we tested whether PKB was activated in TRANCE-stimulated osteoclasts and dendritic cells. An increase in the phosphorylated form of PKB was observed after 5 minutes of TRANCE stimulation in both osteoclasts (FIG. 1A) and dendritic cells (FIG. 1B), indicating that TRANCE indeed induces PKB activation. PKB activity subsided by 60 minutes in osteoclasts whereas it was sustained for greater than 3 hours in dendritic cells. Taken together, TRANCE can induce a variety of signaling pathways implicated in cell survival including ERK, NF-κB and PKB in osteoclasts and dendritic cells.

Figure 2B:
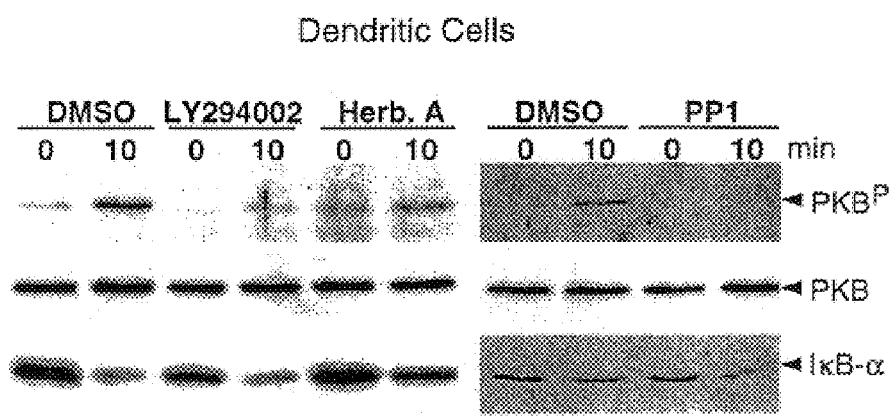
Figure 3B:
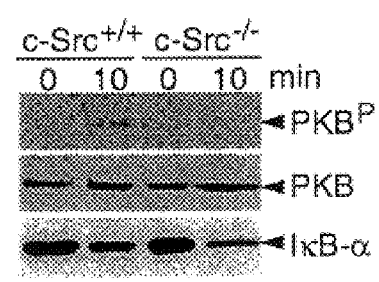
Figure 3C:
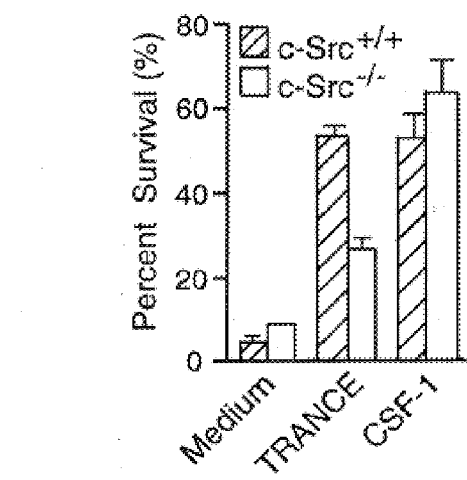

PKB activation by TRANCE is dependent on Src-family kinases and PI3-kinase. To further understand the mechanism by which TRANCE activates PKB, we tested the ability of various inhibitors to block TRANCE-mediated PKB activation in osteoclasts and dendritic cells. PKB is activated when recruited by its pleckstrin homology domain to PI3-kinase-modified lipids (phosphatidylinositol-(3,4,5)-triphosphate and phosphatidylinositol-(3,4)-bisphosphate) in the plasma membrane and it is consequently phosphorylated by PDK1 and PDK2 which are also recruited to the membrane by their PH domains (reviewed in (Coffer, et al., Biochem. J., 335:1–13, 1998)). PKB activation, determined by measuring its phosphorylated form, was inhibited in both osteoclasts (FIG. 2A) and dendritic cells (FIG. 2B) pretreated with the PI3-kinase-specific inhibitor LY294002. Interestingly, herbimycin A, a general PTK inhibitor, and PP1, a specific inhibitor for Src-family kinases, also blocked TRANCE-induced PKB activation (FIG. 2A). MEK inhibitor PD98059, however, failed to inhibit TRANCE-induced PKB activation (data not shown). In addition, neither LY294002, herbimycin A, nor PP1 significantly affected NF-κB activation as measured by IκB-α degradation (FIGS. 2A and 2B) demonstrating their respective specificity. These results provide evidence that TRANCE signaling regulates PKB activity through Src-family- and PI3-kinases in osteoclasts and dendritic cells.

c-Src is ubiquitously expressed in a variety of tissues yet c-Src-deficient mice specifically suffer from osteopetrosis due to defects in osteoclasts (Soriano, et al., supra, 1991). Osteoclasts derived from c-Src–/– cannot resorb bone, fail to form ruffled borders, and have a disrupted cytoskeletal architecture (Boyce, et al., J. Clin. Invest., 90:1622–1627, 1992; Soriano, et al., supra, 1991). Upregulation of c-Src to extremely high levels during osteoclastogenesis may partially explain why osteoclasts are particularly susceptible to a deficiency in c-Src (Lacey, et al., supra, 1998). TRANCE can also induce morphological changes in osteoclasts and enhance bone resorption (Fuller, et al., supra, 1998). These studies, taken together with our results showing that Src-family kinase-specific inhibitor, PP1, inhibited TRANCE-induced PKB activation, suggested that c-Src itself may play a key role in TRANCE-R signaling, at least in osteoclasts. In support of this, TRANCE induced c-Src kinase activity (approximately 2 fold) in osteoclasts and dendritic cells (FIG. 3A). However, there was no detectable c-Src kinase activity in TRANCE-treated macrophages (FIG. 3A) despite a significant activation of NF-κB in these cells consistent with low levels of c-Src protein in macrophages compared with osteoclasts (Lacey, et al., supra, 1998) or dendritic cells. Moreover, activation of PKB, but not activation of NF-κB, was substantially reduced in TRANCE-treated c-Src–/– osteoclasts compared with wild-type osteoclasts (FIG. 3B). Therefore, these data indicate that c-Src kinase activation induced by TRANCE is necessary for PKB activation in osteoclasts. PKB activation, however, was not significantly reduced in dendritic cells from c-Src–/–mice (FIG. 3B). Since PP1 inhibited TRANCE-induced PKB activation in dendritic cells other Src-family kinases may compensate for the loss of c-Src in these cells. These results are consistent with the phenotype of c-Src-deficient mice which exhibit defects specifically in osteoclasts but not in other cell types (Soriano, et al., supra, 1991).

Figure 3D:
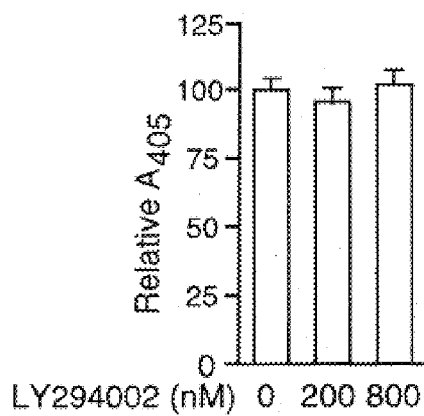
Figure 3E:
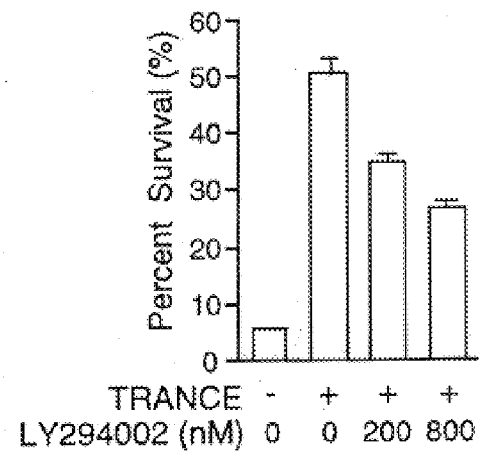

Previous studies showed that PKB is involved in survival signals by a variety of growth factors and cytokines. Therefore, we attempted to determine the role of PKB in TRANCE-induced osteoclast survival. LY294002, at concentrations that did not inhibit osteoclast differentiation (FIG. 3D), significantly reduced cell survival promoted by TRANCE in a dose-dependent manner (FIG. 3E). TRANCE-induced survival was also reduced in c-Src–/– osteoclasts compared to wild-type controls (FIG. 3D) supporting the notion of a c-Src-dependent anti-apoptotic pathway. Cell survival promoted by CSF-1, however, was not reduced in c-Src–/– osteoclasts indicating that a deficiency in c-Src does not impair all anti-apoptotic-signaling pathways. In conclusion, TRANCE activates c-Src or Src-family kinases and PI3-kinase which promote cell survival and induce PKB activation.

The TRANCE-R and TRAF6 associates with c-Src family kinases. The results shown above indicate that c-Src or Src-family kinases play a role in TRANCE-R signaling. To better define the mechanism by which c-Src is activated by the TRANCE-R, we first tested the potential of c-Src to associate with the TRANCE-R/TRAF signaling complex in co-transfection experiments in 293T cells. In this transient transfection system, overexpressed TRANCE-R constitutively activates downstream signals without ligand stimulation as has been described for other receptors (Wong, et al., supra, 1998). Various FLAG-epitope-tagged TRANCE-R and TRAF proteins were co-expressed with c-Src in 293T cells and their association was tested by determining the presence of c-Src in anti-FLAG immunoprecipitates. c-Src associated with wild-type TRANCE-R (TR-wt) in addition to the TRANCE-R deletion mutants TR-235-358, TR-354-536, and TR-235-559, but not appreciably with TR-532-625 (Numbers denote the amino acid sequences of TRANCE-R) nor TR-ecto, which does not contain any cytoplasmic residues (FIG. 4A). In addition, FLAG immunoprecipitates from 293T cells overexpressing TR-wt, TR-235-358, and TR-354-536 but not TR-532-625 or TR-ecto, were associated with an endogenous PTK activity (FIG. 4B). As illustrated in FIG. 4C, c-Src associated with regions of the TRANCE-R that were previously shown to interact with TRAF6 but failed to associate with regions that were shown to interact with only TRAF1, TRAF2, TRAF3, or TRAF5 (Wong, et al., supra, 1998; Galibert, et al., supra, 1998; Darnay, et al., supra, 1999).

The TRAF domain of TRAF6 (amino acids 289–530) but not the N-terminus of TRAF6 (amino acids 1–289) interacted with c-Src, when co-expressed showing that the association between TRAF6 and c-Src appears dependent on TRAF domain. Taken together with the consensus that TRAF adapters are required for linking signaling effectors with TNFR family members (Rothe, et al., supra, 1994; Nishitoh, et al., supra, 1998), these results suggest that TRAF6 can mediate the association between TRANCE-R and c-Src. However, we cannot rule out the possibility that c-Src can also directly interact with TRANCE-R or that other adapters are also involved.

The novel finding that c-Src can associate with TRAF6 prompted an examination of its ability to associate with other TRAF family members. c-Src can potentially form complexes with TRAF1 and TRAF3, but not with TRAF2or TRAF5 (data not shown). Therefore, TRAF1 and TRAF3 may, in addition to TRAF6, mediate the association of c-Src with their upstream membrane-bound receptors. Despite the ability of TRAF1 and TRAF3 to associate with TRANCE-R when over-expressed (Wong, et al., supra, 1998; Galibert, et al., supra, 1998), it appears that endogenous TRAF1 and TRAF3proteins in the cell-types used in this study are not able to mediate interaction between TRANCE-R and c-Src.

To determine whether TRANCE-R, TRAF6 and c-Src indeed form a signaling complex in primary cells, and to avoid potential artifacts in an over-expression system, the association of endogenous TRANCE-R with TRAF6 and c-Src was tested in dendritic cells. Dendritic cells were chosen for this study because dendritic cells, but not osteoclasts, showed a consistently high level of surface TRANCE-R; by FACS analysis, the level of surface TRANCE-R on dendritic cells was at least 10–20 fold higher than on osteoclasts (data not shown). The TRANCE-R was immunoprecipitated from TRANCE-treated and non-treated dendritic cells. FIG. 5B shows TRAF6 and c-Src were readily detected in the TRANCE-R complex upon ligand treatment. Furthermore, the receptor complex, when stimulated by TRANCE, acquired PTK activity towards the PTK-specific substrate SAM68 in an in vitro kinase assay. These results show that TRAF6 and c-Src assemble at the TRANCE-R complex in a ligand-dependent manner.

The TRANCE Receptor Regulates c-Src activity through TRAF6. The results shown above indicate that TRANCE-R can activate c-Src or other related PTKs and that c-Src and TRAF6 are recruited to the TRANCE-R in a ligand-dependent manner. Since we observed that the TRANCE-R signaling complex acquires PTK activity upon ligand engagement, we attempted to analyze the requirements for this activity in an over-expression system using 293T cells. FLAG-immunoprecipitates from cells expressing FLAG-tagged wild-type TRANCE-R (TR-wt) or the various deletion mutants which bind TRAF6 and c-Src (FIG. 4), co-precipitated with PTK activity that was able to phosphorylate SAM68 in vitro. This activity was inhibited when TRANCE-R was co-expressed with a kinase inactive point mutant of c-Src(K295M), suggesting that c-Src and/or other Src-family kinases mediate PTK activity by the TRANCE-R (FIG. 4D). To confirm that TRAF6 is the critical link between TRANCE-R and Src-family kinases, TRAF6 (289–530), previously shown to inhibit TRANCE-R-mediated NF-κB activation (Wong, et al., supra, 1998), was tested for its ability to block TRANCE-R-associated PTK activity. As shown in FIG. 4E, TRAF6 (289–530) could reduce the tyrosine kinase activity associated with TRANCE-R immunoprecipitates. These results provide evidence, under these conditions, that PTK activity in the TRANCE-R signaling complex is dependent on Src-family kinases and TRAF6.

Activation of Src-related kinases requires interaction with the receptor or scaffolding/adapter protein which induces an "open" conformation of the kinase (reviewed in (Schwartzberg, et al., Oncogene, 17:1463–1468, 1998). Since TRAF6 interacts with c-Src and appear to link c-Src to the TRANCE-R signaling complex, we speculated that TRAF6 may not only bridge c-Src to TRANCE-R but also induce its activity. Low amounts of c-Src with TRAF6 or vector alone were transfected in 293 cells and c-Src tyrosine kinase activity in vivo was measured using a known target of c-Src, c-Cbl, as a substrate (Tanaka, et al., Nature, 383:528–531, 1996). As shown in FIG. 4E, expression of limiting amounts of c-Src or TRAF6 alone failed to induce c-Cbl tyrosine phosphorylation. Expression of TRAF6 and c-Src together, however, induced substantial c-Cbl tyrosine phosphorylation, indicating that TRAF6 activates c-Src. When c-Src was co-expressed with TRAF6(289–530), which was sufficient to interact with c-Src (FIG. 4), no detectable c-Cbl phosphorylation was observed, suggesting that c-Src activation requires elements within the N-terminal domain of TRAF6 and that its association with TRAF6 is necessary but not sufficient to trigger its activity. Moreover, TRAF6 (289–530) as well as c-Src(K295M), had an inhibitory effect on TRAF6-mediated c-Cbl phosphorylation (FIG. 4E), providing further evidence that TRAF6 requires its N-terminal regulatory domain to induce c-Src kinase activity.

The Src-family kinase Fyn but not Hck interacts with TRAF6. Since Src-family kinases are known to act redundantly in several signaling pathways in most cell types (reviewed in (Schwartzberg, et al., supra, 1998), we hypothesized that other Src-family kinases may also be involved in TRANCE-R-mediated signaling. In support of this hypothesis, TRANCE-mediated PKB activation in dendritic cells was inhibited by PP1 but not blocked in dendritic cells derived from Src–/– mice (see FIG. 3B). Thus, we tested whether FLAG-tagged TRAF6 associates with Fyn and Hck Src-family kinases when over-expressed in 293T cells. Interestingly, TRAF6 associated with Fyn but not with Hck indicating that TRAF6 can associate with some but not all Src-family kinases (data not shown).

Figure 6A:
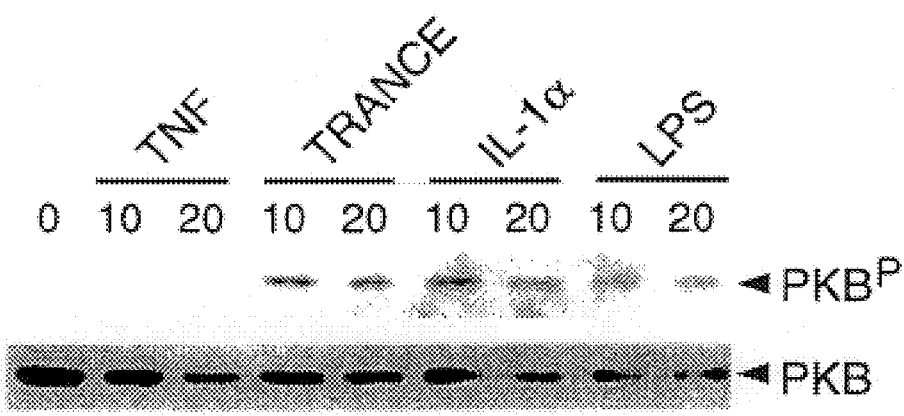
FIG. 6. Cytokine receptors that engage TRAF6 activate PKB through Src-family kinases. (A) Dendritic cells were treated with TNF (10 ng/ml), TRANCE (5 μg/ml), LPS (50 μg/ml), or IL-1α (20 ng/ml) for the indicated times (min). The activation of PKB was determined in whole cell extracts using a phospho-PKB-specific antibody as described in FIG. 1. (B) Dendritic cells were pretreated with vehicle (DMSO) or the Src-family kinase inhibitor, PP1 (10 μM) for 90 minutes followed by a 15 minute treatment with TRANCE (5 μg/ml), LPS (50 μg/ml), or IL-1α (20 ng/ml) or no treatment at all (−). The activation of PKB was determined as described in FIG. 1.
Figure 6B:
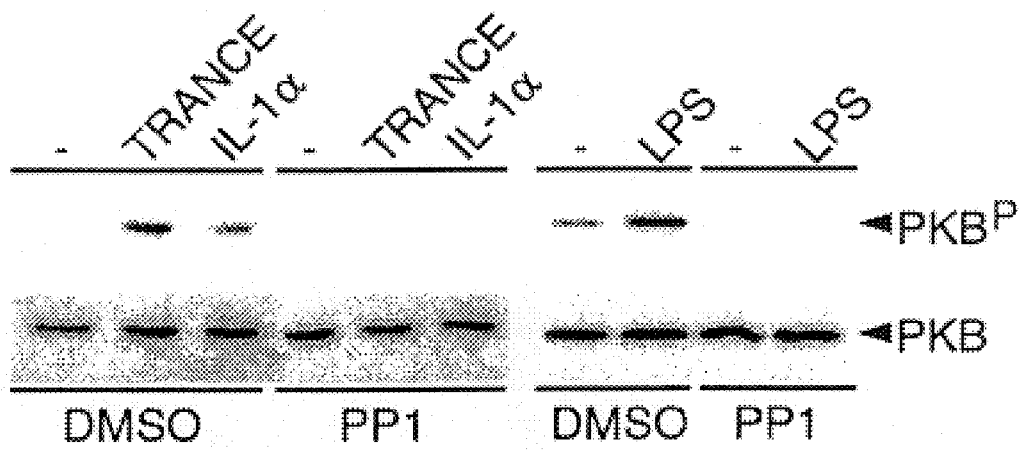

TRAF6 links several signaling receptors to the PKB pathway. TRAF6 has been shown to be involved in signaling by TRANCE-R in addition to other TNFR family members such as CD40 and p75 nerve growth factor receptor, and cytokine receptors including IL-1 receptor and Toll-like receptors (Cao, et al., supra, 1996; Medzhitov, et al., supra, 1998; Zhang, et al., supra, 1999). To test the possibility that TRAF6 is involved in c-Src-mediated PKB activation downstream of other cytokine receptors, we first stimulated dendritic cells with TRANCE, IL-1α, LPS (which signals via toll-like receptors) and CD40L and measured PKB activation. In addition, we stimulated dendritic cells with TNF which does not depend on TRAF6 for its signaling (Cao, et al., supra, 1996). PKB was activated in dendritic cells stimulated with TRANCE, IL-1α and LPS and CD40L (data not shown) but not in cells stimulated with TNF (FIG. 6A). TNF, however, was able to induce substantial IκB degradation confirming the ability of dendritic cells to respond to TNF. Pretreatment of cells with PPI inhibited the activation of PKB by IL-1α and LPS (FIG. 6B), suggesting that PKB activation by other cytokine receptors that engage TRAF6 are also dependent on Src-family kinases. These results suggest that TRAF6 is a multi-functional adapter that may link several cytokine receptors to Src-family kinases.

Discussion

TRAF6 mediates c-Src regulation by TRANCE-R. In this study, an exploration of signaling pathways initiated by TRANCE in osteoclasts and dendritic cells led to two novel conclusions: 1) TNFR family members and other cytokines can regulate PKB through Src-family kinases and PI3-kinase and 2) TRAF6 can associate with and regulate the activity of c-Src. Our results demonstrating that TRAF6 directly activates c-Src provides the first evidence to date describing the regulation of tyrosine kinase-mediated signaling by a TRAF adapter protein.

c-Src and Src-family kinases are activated by receptors, scaffolding proteins and other signaling molecules ultimately leading to the relaxation of intramolecular interactions and the de-repression of kinase activity (Thomas, et al., Annu. Rev. Cell. Dev., 13:513–609, 1997). c-Src associates with TRAF6 through the C-terminal TRAF domain. However, this association was not sufficient to induce c-Cbl phosphorylation (FIG. 4E). The manner in which TRAF6 regulates c-Src is analogous to the regulation of ASK1 and NIK. ASK1 and NIK interact with the TRAF domain of several TRAF family members but their activation requires the presence of functional RING and zinc fingers (Nishitoh, et al., supra, 1998; Song, et al., Proc. Natl. Acad. Sci. U.S.A., 94:9792–9796, 1997). One possibility is that c-Src, upon its interaction with the TRAF domain, phosphorylates residues in the N-terminal region of TRAF6 resulting in the recruitment of additional signaling molecules involved in the phosphorylation of c-Cb1. Another plausible mechanism is that the N-terminal region regulates the activity of c-Src without stably associating with it. Elucidation of how TRAF6 regulates c-Src activity may also reveal a common mechanism by which TRAF adapters regulate their associated signaling molecules.

TRANCE mediated c-Src activation appears to require TRAF6. First, the association of c-Src with the TRANCE-R mapped to regions previously shown to interact with TRAF6 but not other TRAF adapter proteins. Second, regions of TRANCE-R that interact with TRAF6 but not other TRAFs were able to recruit endogenous tyrosine kinase activity. Third, the endogenous tyrosine kinase activity associated with TRANCE-R which appears to be Src-family kinase was also blocked by a dominant negative mutant of TRAF6 (FIG. 4D). Finally, during the preparation of this manuscript, Tak Mak and colleagues reported that osteoclasts from TRAF6 -deficient mice developed normally, but failed to resorb bone, defects similar to those observed in c-Src–/– osteoclasts (Lomaga, et al., Genes Dev., 13:1015–1024, 1999).

PKB Activation by TRANCE-R and other cytokine receptors. TNFR family members promote cell survival by inducing NF-KB activation, a transcription factor that upregulates genes involved in cell survival including cellular-inhibitors of apoptosis (c-IAPs), TRAF proteins (reviewed in Arch, et al., supra, 1998) and Bcl-2 family members. Our results demonstrated that TRANCE and other cytokines that recruit TRAF6 can activate PKB, a kinase that potentiates cell survival by inhibiting several apoptosis-inducing pathways. For example, BAD, a pro-apoptotic Bcl-2 family member, when phosphorylated by PKB, is sequestered into the cytoplasm by the scaffolding protein 14-3-3 and consequently is prevented from interacting with Bcl-2 and Bcl-xL in the mitochondria membrane (Zha, et al., Cell, 87:619–628, 1996). PKB also phosphorylates and inhibits FKHRL1, a Forkhead transcription factor that regulates various apoptosis-inducing genes including Fas ligand (Brunet, et al., Cell, 96:857–868, 1999) and caspase-9, a cell death protease (Cardone, et al., Science, 282:1318–1321, 1998). Therefore, we have identified a novel mode of signaling by which TNFR family members regulate cell survival.

Several cytokines that modulate immune responses activate Src-family kinases through unknown mechanisms. For example, CD40L can activate Lyn in Daudi B-cells and LPS can stimulate Lyn, Fgr and Hck in monocytes. Our results demonstrating that TRAF6 can associate with c-Src or Fyn in co-expression assays and/or primary cells implicate TRAF6 in the regulation of Src-family kinases by several types of signaling receptors that engage TRAF6. TRAF1 and TRAF3also associated with c-Src providing evidence that these adapter molecules function by recruiting Src-family kinases to their upstream receptors. It will be interesting to determine the relevance of the association of TRAF1 and TRAF3with c-Src or Src-family kinases in vivo. Taken together, TRAF6 and possibly TRAF1 and TRAF3 may bridge a variety of cytokine receptors to specific Src-family kinases.

Figure 7:
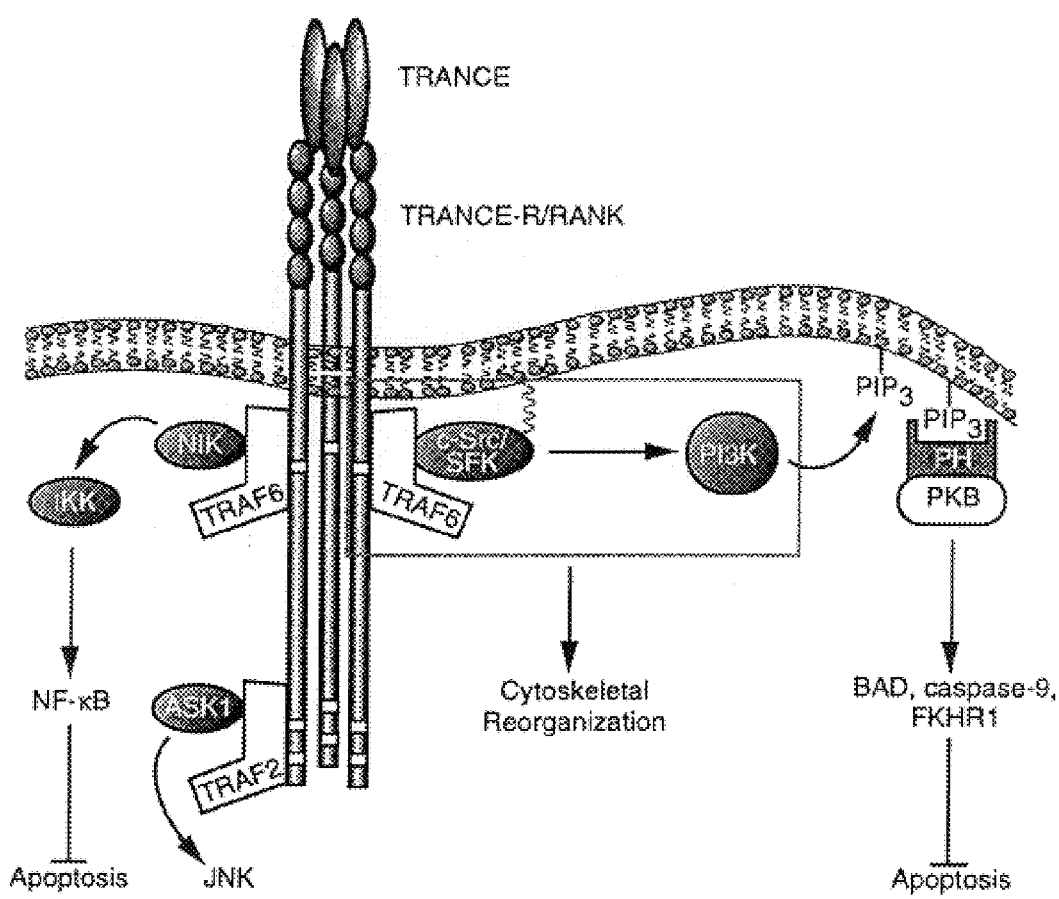
FIG. 7. A model of a novel signaling pathway linking PKB to TRANCE-R through Src-family kinases and PI3-kinase. TRANCE/TRANCE-R (RANK) interactions result in the recruitment of TRAF2 and TRAF6 to distinct regions of the cytoplasmic tail. TRAF6, when bound to a membrane-proximal region, activates NIK, leading to IκB kinase (IKK)-dependent NF-κB activation. TRAF2, which interacts with a distal portion of the TRANCE-R, activates c-Jun N-terminal kinases (JNK) activation via ASK1 (Wong et al., supra, 1997; Darnay et al., supra, 1999). c-Src is also recruited to the TRANCE-R in a ligand dependent manner most likely through TRAF6. c-Src activation, which can be potentiated by TRAF6, is likely to activate PI3-kinase (Thomas et al., Annu. Rev. Cel. Dev. Biol., 13:513–609, 1997) which, in turn, catalyzes the formation of phosphatidylinositol-(3,4,5)-phosphate (PIP$_3$) at the membrane. Protein kinase B (PKB)/Akt, is recruited through its pleckstrin-homology (PH) domain to PIP$_3$ where it is activated and subsequently phosphorylates and inactivates several pro-apoptotic genes including BAD, caspase-9, and FKHR1.

Consequences of Src-family kinase and PI3-kinase activation. Examination of the mechanism activating PKB downstream of the TRANCE-R revealed the involvement of TRAF6, Src-family kinases and PI3-kinase. FIG. 7 presents a model describing the events from the TRANCE-R leading to the activation of PKB. However, the activation of PKB by TRANCE is only one of several downstream pathways initiated by c-Src and PI3-kinase.

Specifically, Src-family kinases are involved in controlling cell spreading, focal adhesion formation and disassembly and membrane ruffling (reviewed in (Thomas, et al., supra, 1997 and Fruman, et al., Annu. Rev. Biochem., 67:481–507, 1998). c-Src performs these functions by inducing the phosphorylation of an array of cytoskeletal proteins such as vinculin, paxillin and adapter molecules such as p130Cas and c-Cbl and kinases such focal adhesion kinase, Pyk2 and PI3-kinase. In osteoclasts, c-Src is critical for the formation of actin rings which allow the cell to seal itself against the bony matrix and resorb bone (Boyce, et al., J. Clin. Invest., 90:1622–1627, 1992; Schwartzberg, et al., supra, 1997). Interestingly, during the preparation of this manuscript, TRANCE was demonstrated to induce actin ring formation (Burgess, et al., J. Cell. Biol., 145:527–538, 1999), which involves cytoskeletal alterations dependent on c-Src (Boyce, et al., supra, 1992). These results are consistent with our data showing that TRANCE directly regulates c-Src activity. Therefore, TRANCE may control osteoclast morphology and bone resorbing capacity by regulating cytoskeletal rearrangements through c-Src. It must be noted, that c-Src kinase activity is not absolutely required for osteoclast-mediated bone resorption since the defects in c-Src-deficient mice can be partially rescued by transgenic expression of c-Src(K295M). However, osteoclasts from mice rescued by the transgene still exhibit defects in morphology and bone density compared with wild-type mice indicating that c-Src kinase activity is important in certain aspects of osteoclast function (Schwartzberg, et al., supra, 1997).

PI3-kinase, when activated by growth factors and cytokines translocates to the plasma membrane where it mediates a variety of effects including cell adhesion, motility, proliferation, growth, differentiation and survival. PI3-kinase is activated when its regulatory subunit (p85) interacts with phosphorylated tyrosine residues on the receptor or receptor-associated proteins. The p85-binding consensus motif YXXM, is not present on TRANCE-R nor on TRAF6 suggesting that another adaptor is responsible for TRANCE-mediated PI3-kinase activation. One potential candidate, the scaffolding protein c-Cbl, which can interact with p85, is dependent on c-Src for its phosphorylation in osteoclasts. Experiments presented here suggest that TRAF6 activates c-Src to phosphorylate c-Cbl suggesting that this complex, alone, may be sufficient in activating PI3-kinase. However, further studies are required to determine the signaling events from TRANCE-R leading to PI3-kinase activation. In addition, mechanisms regulating TRANCE-mediated PI3-kinase activation may differ between cell types since PI3-kinase can be regulated by a multitude of signaling pathways.

The study of signal transduction pathways induced by TRANCE in osteoclasts and dendritic cells revealed that the TRANCE-R complex regulates Src-family kinase activity through TRAF6 leading to PI3-kinase and PKB activation, a new signaling cascade described for a TNFR family member. PKB activation, together with the activation of ERK and NF-κB are likely to be responsible for TRANCE-mediated survival. The signaling events responsible for PKB activation including TRAF6, Src-family kinases and PI3-kinase, may also mediate morphological changes triggered by TRANCE in osteoclasts. Since TRAF6 is a common adaptor protein, other cytokine receptors may also cross-talk to Src-family kinase-mediated signaling. Our results provide insight into how TRANCE regulates osteoclasts and dendritic cells and may have implications in diseases of bone or the immune system.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values are approximate, and are provided for description.

All patents, patent applications, publications, and other materials cited herein are hereby incorporated herein reference in their entireties.

We claim:

1. A method of screening for an inhibitor of signaling from a TRANCE receptor, which method comprises comparing:
   (a) a signal when signaling from a TRANCE receptor in a cell is induced in the presence of a candidate compound; and
   (b) the signal when signaling from the TRANCE receptor in the cell is induced in the absence of the candidate compound,
   wherein the signal is selected from the group consisting of AKT/PKB phosphorylation, c-Src phosphorylation, and PI3 kinase activity, and
   inhibition of the signal in the presence of the candidate compound indicates that the candidate compound is an inhibitor of signaling from a TRANCE receptor.

2. The method according to claim 1, wherein signaling from the TRANCE receptor is induced according to a method that comprises contacting the cell with TRANCE.

3. The method according to claim 1, wherein signaling from the TRANCE receptor is induced according to a method that comprises contacting the cell with a TRANCE agonist.

4. The method according to claim 1, wherein the signal comprises AKT/PKB phosphorylation.

5. The method according to claim 1, wherein the signal comprises c-Src phosphorylation.

6. The method according to claim 1, wherein the signal comprises PI3 kinase activity.

7. The method according to claim 1, wherein the cell is an osteoclast precursor cell.

8. The method according to claim 1, wherein the cell is an osteoclast.

9. The method according to claim 1, wherein the cell is a dendritic cell.

10. A method of screening for an agonist of signaling from a TRANCE receptor, which method comprises comparing:
    (a) a signal in a cell contacted with a candidate compound, which cell expresses a TRANCE receptor; and
    (b) the signal in the cell contacted with the candidate compound, when the TRANCE receptor is inhibited,
    wherein the signal is selected from the group consisting of AKT/PKB phosphorylation, c-Src phosphorylation, and PI3 kinase activity, and
    an increase of the signal when the cell expresses the TRANCE receptor compared to when the TRANCE receptor is inhibited indicates that the candidate compound is an agonist of TRANCE-induced signaling.

11. The method according to claim 10, wherein the signal comprises AKT/PKB phosphorylation.

12. The method according to claim 10, wherein the signal comprises c-Src phosphorylation.

13. The method according to claim 10, wherein the signal comprises PI3 kinase activity.

14. The method according to claim 10, wherein the cell is an osteoclast precursor cell.

15. The method according to claim 10, wherein the cell is an osteoclast cell.

16. The method according to claim 10, wherein the cell is a dendritic cell.

17. A method of screening for an agonist of AKT/PKB phosphorylation, which method comprises comparing:
    (a) a signal in a cell contacted with a candidate compound, which cell expresses a TNFR family receptor for a cytokine, and which signal is selected from the group consisting of c-Cbl phosphorylation, SAM68 phosphorylation and c-Src phosphorylation; and
    (b) the signal in the cell contacted with the candidate compound when the TNFR family receptor is inhibited,
    wherein an increase of the signal when the cell expresses a TNFR family receptor compared to when the TNFR family receptor is inhibited indicates that the candidate compound is an agonist of AKT/PKB phosphorylation.

18. The method according to claim 17, wherein the cytokine receptor is selected from the group consisting of TRANCE-R/RANK, interleukin (IL)-1α receptor, CD40, and p75 nerve growth factor receptor.

19. The method according to claim 17, wherein the signal comprises c-Cbl phosphorylation.

20. The method according to claim 17, wherein the signal comprises SAM68 phosphorylation.

21. The method according to claim 17, wherein the signal comprises c-Src phosphorylation.

22. A method of screening for an inhibitor of AKT/PKB activation, which method comprises comparing:
    (a) a signal in a cell contacted, in the presence of a candidate compound, with a cytokine,
       which signal is selected from the group consisting of c-Cbl phosphylation, SAM68 phosphorylation and c-Src phosphorylation; and
    (b) the signal in the cell contacted with the cytokine in the absence of the candidate compound,
    wherein inhibition of the signal in the presence of the candidate compound indicates that the candidate compound is an inhibitor of AKT/PKB phosphorylation.

23. The method according to claim 22, wherein the cytokine is selected from the group consisting of TRANCE, interleukin (IL)-1α, CD40, and p75 nerve growth factor.

24. The method according to claim 22, wherein the cell is a dendritic cell.

25. The method according to claim 21, wherein the signal comprises c-Cbl phosphorylation.

26. The method according to claim 22, wherein the signal comprises SAM68 phosphorylation.

27. The method according to claim 21, wherein the signal comprises c-Src phosphorylation.

28. A method of screening for an enhancer of signaling from a TRANCE receptor, which method comprises comparing:
    (a) a signal when signaling from a TRANCE receptor is induced in the presence of a candidate compound; and (b) the signal when signaling from the TRANCE receptor is induced in the absence of the candidate compound, wherein the signal is selected from the group consisting of AKT/PKB phosphorylation, c-Src phosphorylation and PI3 kinase activity, and an increase of the signal in the presence of the candidate compound indicates that the candidate compound enhances signaling from a TRANCE receptor.

29. The method according to claim 28, wherein signaling from the TRANCE receptor is induced according to a method that comprises contacting the cell with TRANCE.

30. The method according to claim 28, wherein signaling from the TRANCE receptor is induced according to a method that comprises contacting the cell with a TRANCE agonist.

31. The method according to claim 28, wherein the signal comprises AKT/PKB phosphorylation.

32. The method according to claim 28, wherein the signal comprises c-Src phosphorylation.

33. The method according to claim 28, wherein the signal comprises PI3 kinase activity.

34. A method of screening for an enhancer of AKT/PKB phosphorylation, which method comprises comparing:

(a) a signal in a cell contacted, in the presence of a candidate compound, with a cytokine, which signal is selected from the group consisting of c-Cbl phosphorylation, SAM68 phosphorylation and c-Src phosphorylation; and (b) the signal in the cell contacted with the cytokine in the absence of the candidate compound, wherein an increase of the signal in the presence of the candidate compound indicates that the candidate compound is an agonist of AKT/PKB phosphorylation.

35. The method according to claim 34, wherein the cytokine receptor is selected from the group consisting of TRANCE-R/RANK, interleukin (IL)-1$\alpha$ receptor, CD40 and p75 nerve growth factor receptor.

36. The method according to claim 34 wherein the signal comprises c-Cbl phosphorylation.

37. The method according to claim 34 wherein the signal comprises SAM68 phosphorylation.

38. The method according to claim 34 wherein the signal comprises c-Src phosphorylation.

39. The method according to claim 34 wherein the cell is a dendritic cell.

* * * * *